United States Patent
Escano

(10) Patent No.: US 7,666,221 B2
(45) Date of Patent: *Feb. 23, 2010

(54) LOCK MODULAR GRAFT COMPONENT JUNCTIONS

(75) Inventor: Arnold M. Escano, Santa Clara, CA (US)

(73) Assignee: Endovascular Technologies, Inc., Menlo Park, CA (US)

(*) Notice: Subject to any disclaimer, the term of this patent is extended or adjusted under 35 U.S.C. 154(b) by 1233 days.

This patent is subject to a terminal disclaimer.

(21) Appl. No.: 10/222,728

(22) Filed: Aug. 16, 2002

(65) Prior Publication Data

US 2003/0229389 A1 Dec. 11, 2003

Related U.S. Application Data

(63) Continuation-in-part of application No. 10/090,472, filed on Mar. 4, 2002, now Pat. No. 7,226,474, which is a continuation-in-part of application No. 09/562,595, filed on May 1, 2000, now Pat. No. 7,135,037.

(60) Provisional application No. 60/360,323, filed on Feb. 26, 2002.

(51) Int. Cl.
*A61F 2/06* (2006.01)
*A61M 29/00* (2006.01)

(52) U.S. Cl. .................................. 623/1.36

(58) Field of Classification Search ....... 623/1.11–1.36, 623/1.37, 1.38, 1.39; 606/191, 194, 198
See application file for complete search history.

(56) References Cited

U.S. PATENT DOCUMENTS

| | | |
|---|---|---|
| 3,657,744 A | 4/1972 | Ersek |
| 4,140,126 A | 2/1979 | Choudhury |
| 4,562,596 A | 1/1986 | Kornberg |
| 4,787,899 A | 11/1988 | Lazarus |
| 5,064,435 A | 11/1991 | Porter |
| 5,489,295 A | 2/1996 | Piplani et al. |
| 5,562,724 A | 10/1996 | Vorwerk et al. |
| 5,575,817 A | 11/1996 | Martin |
| 5,609,627 A | 3/1997 | Goicoechea et al. |
| 5,628,788 A | 5/1997 | Pinchuk |

(Continued)

FOREIGN PATENT DOCUMENTS

DE 9319267 4/1994

(Continued)

OTHER PUBLICATIONS

Chuter, et al., "Transfemoral Endovascular Aortic Graft Placement," Journal of Vascular Surgery, vol. 18, No. 2, Aug. 1993, pp. 185-197.

(Continued)

*Primary Examiner*—Vy Q Bui
(74) *Attorney, Agent, or Firm*—Brooks, Cameron & Huebsch, PLLC

(57) ABSTRACT

The present invention embodies an endovascular graft having an attachment frame connection mechanism that allows placement of the main body component in vasculature in combination with limb components. Various limb component-to-main body component attachment mechanisms are provided which ensure a reliable bond while facilitating a smaller delivery profile.

39 Claims, 25 Drawing Sheets

U.S. PATENT DOCUMENTS

| | | | |
|---|---|---|---|
| 5,632,772 A | 5/1997 | Alcime et al. | |
| 5,639,278 A | 6/1997 | Dereume et al. | |
| 5,653,743 A | 8/1997 | Martin | |
| 5,676,696 A | 10/1997 | Marcade | |
| 5,683,449 A | 11/1997 | Marcade | |
| 5,683,450 A | 11/1997 | Goicoechea et al. | |
| 5,686,451 A | 11/1997 | Kristianson et al. | |
| 5,713,917 A | 2/1998 | Leonhardt et al. | |
| 5,716,365 A | 2/1998 | Goicoechea et al. | |
| 5,718,724 A | 2/1998 | Goicoechea et al. | |
| 5,723,004 A | 3/1998 | Dereume et al. | |
| 5,741,325 A | 4/1998 | Chaikof et al. | |
| 5,755,769 A | 5/1998 | Richard et al. | |
| 5,776,180 A | 7/1998 | Goicoechea et al. | |
| 5,800,508 A | 9/1998 | Goicoechea et al. | |
| 5,824,037 A | 10/1998 | Fogarty et al. | |
| 5,824,042 A | 10/1998 | Lombardi et al. | |
| 5,855,598 A | 1/1999 | Pinchuk | |
| 5,916,263 A | 6/1999 | Goicoechea et al. | |
| 5,938,696 A | 8/1999 | Goicoechea et al. | |
| 5,957,974 A | 9/1999 | Thompson et al. | |
| 5,993,481 A | 11/1999 | Marcade et al. | |
| 6,015,431 A | 1/2000 | Thornton et al. | |
| 6,051,020 A | 4/2000 | Goicoechea et al. | |
| 6,077,297 A | 6/2000 | Robinson et al. | |
| 6,099,558 A | 8/2000 | White et al. | |
| 6,102,938 A | 8/2000 | Evans et al. | |
| 6,102,940 A | 8/2000 | Robichon et al. | |
| 6,110,198 A | 8/2000 | Fogarty et al. | |
| 6,117,167 A | 9/2000 | Goicoechea et al. | |
| 6,120,522 A | 9/2000 | Vrba et al. | |
| 6,123,722 A | 9/2000 | Fogarty et al. | |
| 6,149,682 A | 11/2000 | Frid | |
| 6,162,246 A | 12/2000 | Barone | |
| 6,165,213 A | 12/2000 | Goicoechea et al. | |
| 6,302,906 B1 | 10/2001 | Goicoechea et al. | |
| 6,773,454 B2 * | 8/2004 | Wholey et al. | 623/1.15 |
| 2002/0019659 A1 | 2/2002 | Goicoechea et al. | |

FOREIGN PATENT DOCUMENTS

| | | |
|---|---|---|
| FR | 2 678 508 | 1/1993 |
| SU | 660689 | 5/1979 |
| SU | 1217402 | 3/1986 |
| SU | 1457921 | 2/1989 |
| WO | WO96/39999 | 12/1996 |

OTHER PUBLICATIONS

Parodi, et al. "Transfemoral Intraluminal, Graft Implantation-for Abdominal Aortic Aneurysms," Annals of Vacular Surgery, vol. 5, No. 6, 1991, pp. 491-499.

Criado et al., "Transluminal Recanalization, Angioplasty and Stenting in Endovascular Surgery: Techniques and Applications," From Greenhalgh, Vascular and Endovascular Surgical Techniques, $3^{rd}$ Edition, 1994, pp. 49-70.

Marin et al., "Endoluminal Stented Graft Aorto-Bifemoral Reconstruction," from Greenhalgh, Vascular and Endovascular Surgical Techniques, 3.sup.rd Edition, 1994, pp. 100-104.

May et al., "Transluminal Placement of a Prosthetic Graft-Stent Device for Treatment of Subclavian Artery Aneurysm," Journal of Vascular Surgery, vol. 18, No. 6, Dec. 1993, pp. 1056-1059.

Chuter, T., "Bifurcated Endovascular Graft Insertion for Abdominal Aortic Aneurysm," from Greenhalgh, Vascular and Endovascular Surgical Techniques, 3.sup.rd Edition, 1994, pp. 92-99.

Moore, W.S., "Transfemoral Endovascular Repair of Abdominal Aortic Aneurysm Using the Endovascular Graft System Device," from Greenhalgh, Vascular and Endovascular Surgical Techniques, 3.sup.rd Edition, 1994, pp. 78-91.

* cited by examiner

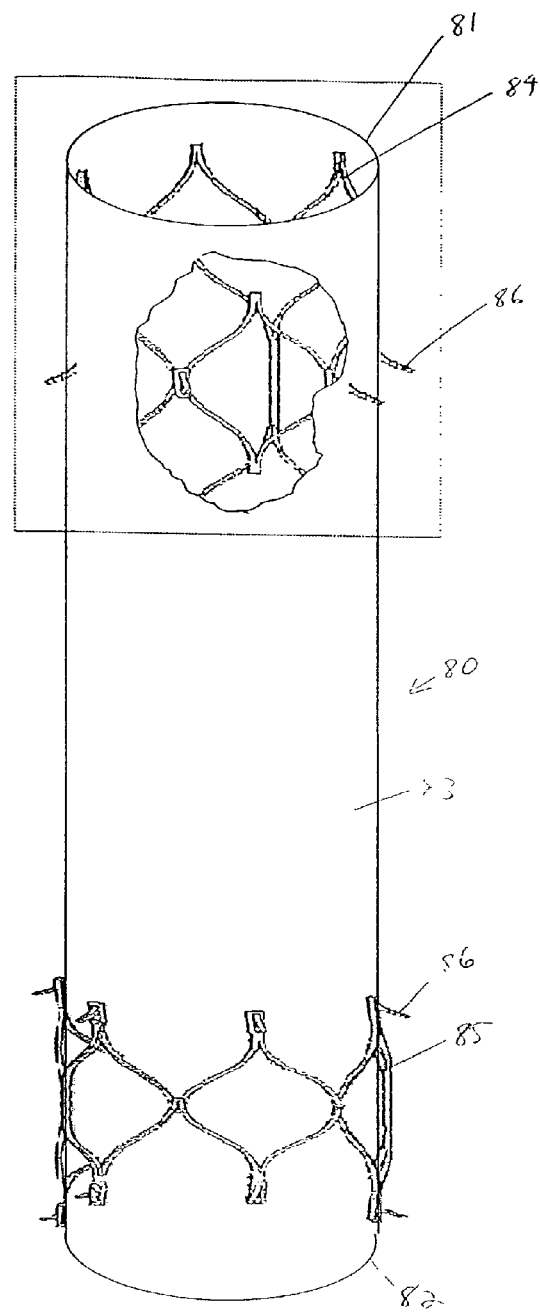
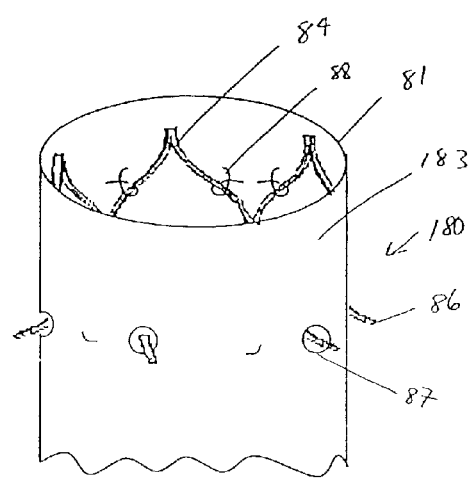
FIG. 1
FIG. 2

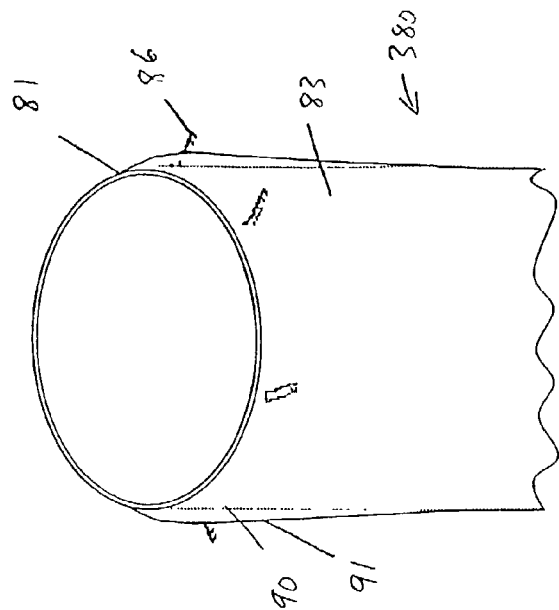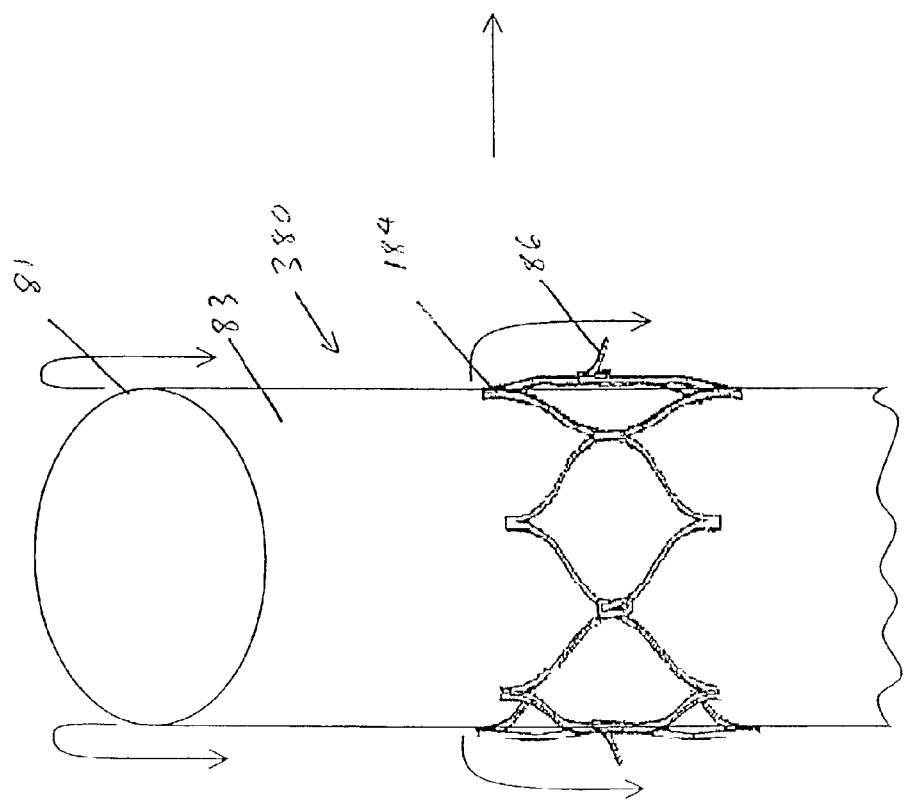
FIG. 6

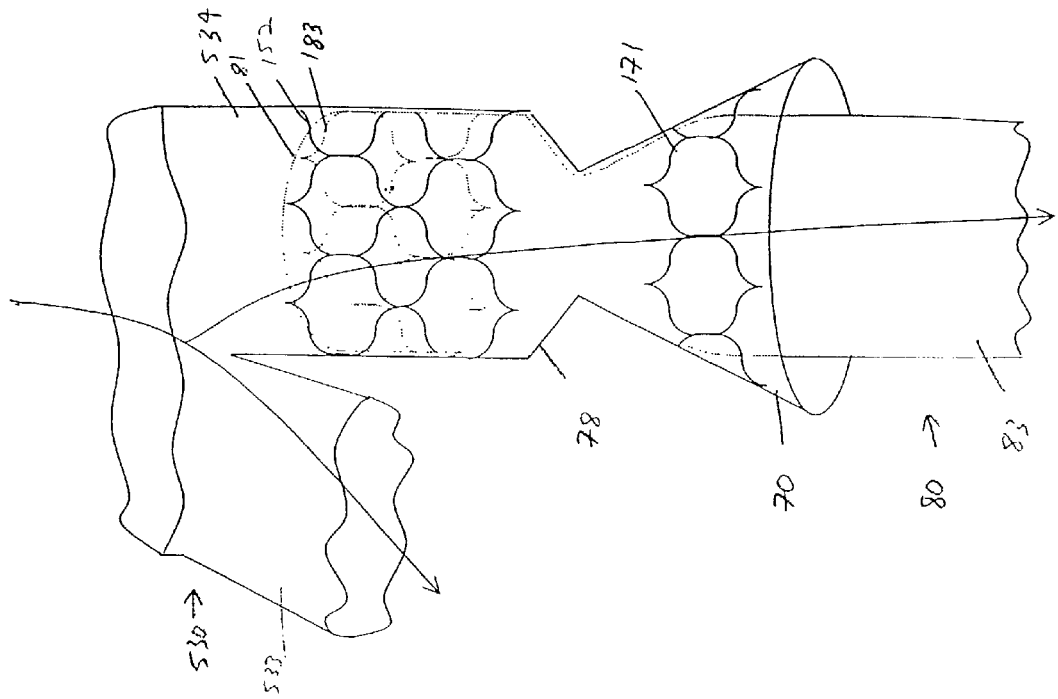
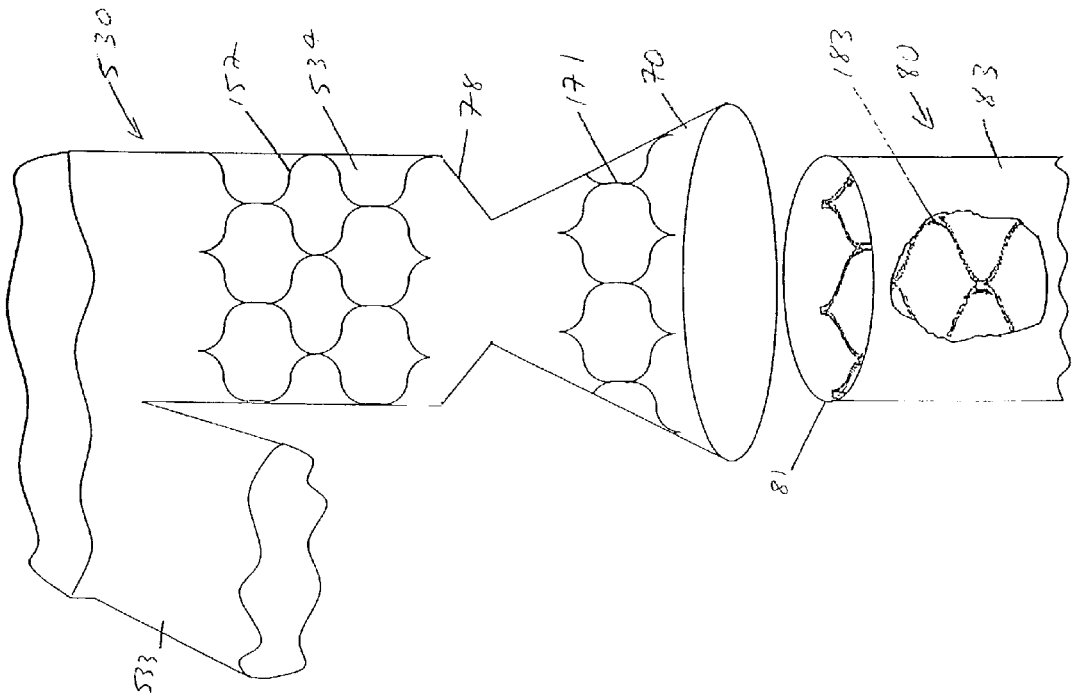

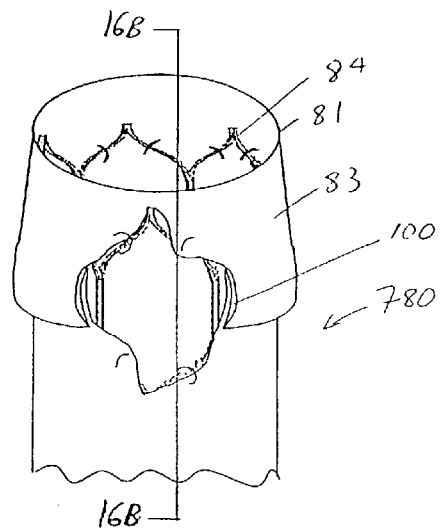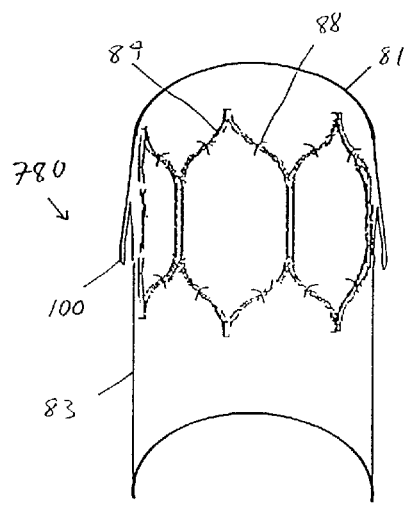
FIG. 16A　　　　　　　　　FIG. 16B
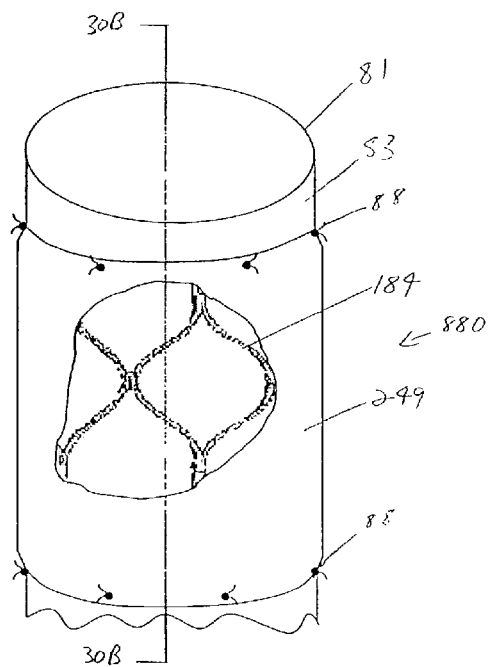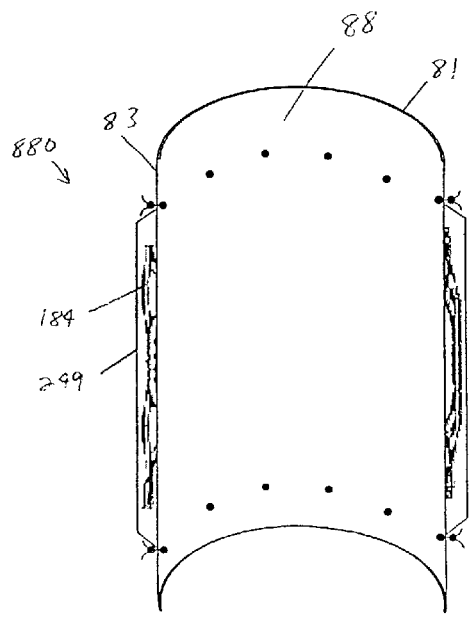
FIG. 17A　　　　　　　　　FIG. 17B

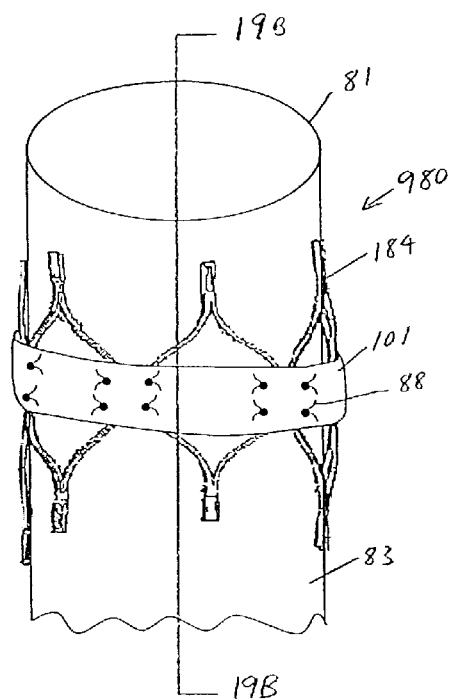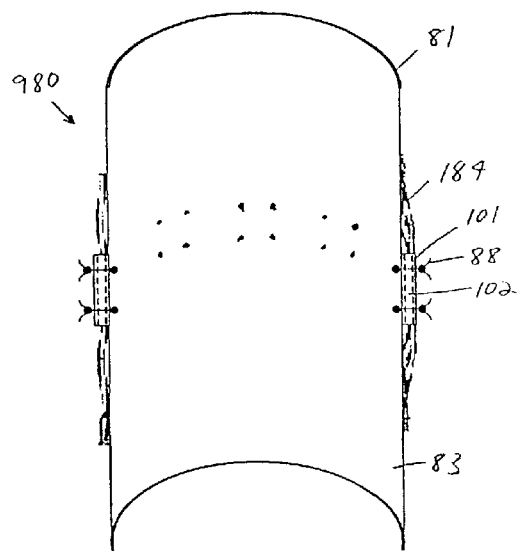
FIG. 19A
FIG. 19B
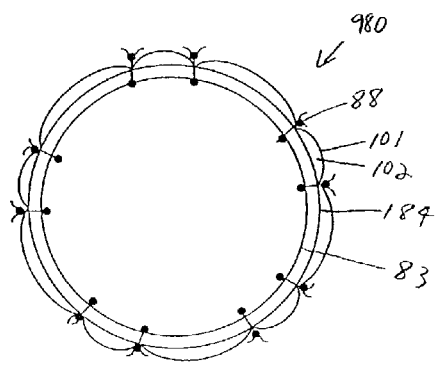
FIG. 19C

LOCK MODULAR GRAFT COMPONENT JUNCTIONS

This application is a continuation-in-part of U.S. application Ser. No. 10/090,472, filed Mar. 4, 2002 which is a continuation-in-part of U.S. application Ser. No. 09/562,595, filed May 1, 2000. This application claims the benefit of U.S. Provisional Application Serial No. 60/360,323, filed Feb. 26, 2002, entitled Endovascular Grafting Device, which contents are incorporated herein by reference in its entirety.

BACKGROUND OF THE INVENTION

This invention relates to methods for delivering and deploying an endovascular graft within the vasculature of a patient and more specifically to a modular grafting system used to treat vasculature.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching the individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Drawbacks with current methods can be categorized in three ways; drawbacks associated with delivery and deployment of the individual endovascular graft components, drawbacks associated with the main body portion, and drawbacks associated with securing the limb portions to the main body portion.

The drawbacks of current methods of joining the limb components of a modular endovascular graft to the main graft component include disruption of the junction over time and leakage at the connection site of the components. The junctions conventionally used in the art may depend upon friction between the overlapping components to hold them in place relative to each other. In other cases, the overlapping portion of one component may be adapted to form a frustoconical shape compatible with the overlapping portion of the other component. This serves to enhance the frictional connection between the components and provides a degree of mechanical joining. However, certain of these junctions relies primarily upon radial pressure of a stent to accomplish the joint-seal between the components and may be disrupted by the high shear forces generated by the blood flow and shrinkage of the aneurysm sac during the natural healing process. Once the junction between modular components of an endovascular graft has been disrupted, blood may flow into the aneurysm sac, a condition known as "endoleak" that can cause repressurization of the aneurysm that leads to death or severe injury to the patient.

Furthermore, even if the junction between the components is not disrupted, leakage may still occur. The limb components used in friction-fit designs often are composed of a stent-like exoskeleton over a layer of graft material. This means that the seal is between the graft material of the limb support portion of the main body component and the stent structure of the limb component. Since the stent is not a closed structure, it is still possible for blood to leak between the limb component and the main body component.

With regard to the method of joining the limb components of a modular endovascular graft to the main body component, there therefore exists a need for structure and a method that provides a leak-proof seal that will not be disrupted by blood flow or physiologic remodeling over time.

The devices and methods of the present invention address these and other needs.

SUMMARY OF THE INVENTION

Briefly and in general terms, the present invention embodies an endovascular graft composed of individual components delivered individually and assembled in-vivo and methods for delivering, deploying and assembling the same.

Throughout this specification, the term "proximal" shall mean "nearest to the heart", and the term "distal" shall mean "furthest from the heart." Additionally, the term "ipsi-lateral" shall mean the side for example of the limb of a bifurcated graft which is deployed using the same path through the vasculature that was used to deploy the main body component, and the term "contra-lateral" shall mean the side for example of the limb of a bifurcated graft which is deployed using a second path through the vasculature which is catheterized after the main body component has been deployed. Furthermore, the term "inferior" shall mean "nearest to the technician", and the term "superior" shall mean "farthest from the technician."

In one aspect, the invention is directed toward limb components and methods of attaching them to the main body component of an endovascular graft that provide a leak-resistant seal between the graft material of the components that will not be disrupted by blood flow or physiologic remodeling over time. Two primary concepts are contemplated; attachment via hooks or barbs that penetrate the graft material components and mechanical attachment that does not require penetration of the graft material of the components.

In a preferred embodiment of the invention, the limb component is attached to the limb portion of the main body component by a frame or self-expanding stent at the proximal or superior end of the limb component that is either inside the limb component or external the limb component with graft material folded over it. The limb can be manufactured with the hooks already through its graft. When the proximal end of the limb component is inserted and deployed within the distal end of the limb support portion of the main body component, radially extending components in the form, for example, of hooks or barbs incorporated within the self-expanding stent penetrate the graft material of the limb support portion of the main body component to form a graft-to-graft bond.

Trauma and wear on the graft material may be reduced in several ways. The limb component can have pre-fabricated holes cut in the graft that allow the hooks and barbs to pass through, thereby reducing trauma and wear to the limb component graft.

The bond between the limb component and limb support portion of the main body component can be strengthened in several ways. Tufting or the placement of fuzzy yarn on the outside of the limb component graft and inside the limb support portion of the main body component promotes blood clotting which forms a better seal. Additionally, the stent hooks and barbs can be angled caudally (toward the feet) such that the blood flow causes better penetration of the graft material and resistance to axial displacement of the components.

In an alternate embodiment of the invention, the limb component is attached to the limb support portion of the main body component by a mechanical joint formed between the distal end of the limb support portion and the proximal end of the limb component that utilizes the natural blood flow in the vessel to strengthen the bond. The distal end of the limb support portion of the main body component has an inner cuff, inward taper, or inner flap that is designed to receive the limb component when it is deployed. Conversely, the limb component proximal end has a stent with outward protrusions, outward taper, or outer flap that engages the inner side of the limb support portion distal end when it is deployed. The axial pressure of the natural blood flow inside the vessel helps to maintain the joint between the components. Additionally, the distal end of the limb support portion of the main body component may contain a tapered inner sleeve that facilitates funneling blood flow into the attached limb component.

In another alternate embodiment, the limb component is attached to the limb support portion of the main body component by a radially adjustable structure or a "lasso" that tightens around the limb component as it is deployed within the limb support portion. The "lasso" consists of a thread connected to two slip-knots; one located at the distal end of the limb support portion of the main body component and the other located proximal of the first. When the proximal end of the limb component is deployed within the limb support portion of the main body component, the radial expansion of the self-expanding frame or stent at the proximal end of the limb component causes the most proximal slip-knot on the limb support portion to expand, which, in turn, tightens the slip-knot at the distal end of the limb support portion around the limb component.

In another alternate embodiment of the invention, the limb component is attached to the limb support portion of the main body component by a frame or stent at the proximal end of the limb component or the distal end of the limb support portion of the main body component. The frame or stent has radially extending components that extend past the end of the graft material and may be located inside or external the limb component or limb support portion. When the end of the limb component or limb support portion containing the frame or stent is inserted and deployed within the second component, the radially extending components in the form, for example, of hooks or barbs, penetrate the graft material of the second component to form a graft-to-graft bond. Radially extending components may also be incorporated at the proximal end of the main body component and the distal end of the limb component, the hooks or barbs of the radially extending components extending past the graft material to facilitate embedding the graft component in the body lumen. It is contemplated that the radially extending components may be self-expanding or expanded by a balloon using methods known in the art. It is further contemplated that the main body component may have a support frame or stent at the distal end of the limb support portion to provide additional support. The support frame or stent may be either inside or external the limb support portion and either self-expanding or balloon expandable.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view, depicting a limb component and attachment stents of the present invention with the graft material partially removed to show the internal stent;

FIG. 2 is a partial perspective view of an alternate embodiment of the limb component depicted in FIG. 1 with pre-fabricated holes for the limb attachment stent in the graft material;

FIG. 5 is a partial perspective view of an alternate embodiment of the limb component depicted in FIG. 1 with the proximal end of the graft material folded over the external limb attachment stent and attached to the limb component;

FIG. 12A is a partial perspective view of an alternate embodiment of the main body and limb components of the present invention where the limb support portion of the main body component has a tapered portion and a "bell-bottom" distal portion with support stents and the limb component has an internal support stent;

FIG. 12B is a partial perspective view depicting the joint formed when the limb component shown in FIG. 12A is deployed within the limb support portion of the main body component shown in FIG. 12A;

FIG. 16A is a partial perspective view depicting the proximal end of a limb component of the present invention where the graft material is folded over itself to provide additional support for the area where there is the largest separation between stent struts and the graft material is partially removed to show the internal stent;

FIG. 16B is a cross-sectional view along line 16B-16B of FIG. 16A;

FIG. 17A is a partial perspective view depicting the proximal end of a limb component of the present invention with a graft material patch attached over an unattached external stent and the graft material patch partially removed to show the stent;

FIG. 17B is a cross-sectional view along line 17B-17B of FIG. 17A;

FIG. 19A is a partial perspective view depicting the proximal end of a limb component of the present invention where a graft belt is attached over an external stent;

FIG. 19B is a cross-sectional view along line 19B-19B of FIG. 19A;

FIG. 19C is a view of the limb component depicted in FIG. 19A from the proximal end;

DETAILED DESCRIPTION OF THE PREFERRED EMBODIMENTS

Figure 4:
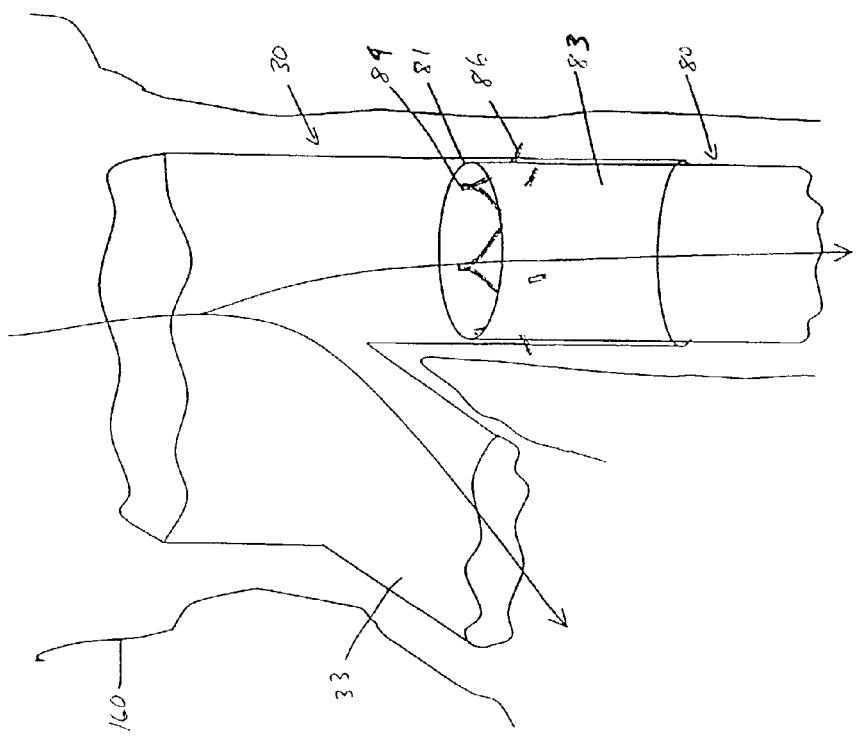
FIG. 4 is a side elevation, partial cross-sectional view of a main body component already implanted at the treatment site with the limb support portions floating freely and the limb component depicted in FIG. 1 deployed inside one of the limb support portions.

The present invention relates to an endovascular graft which is assembled in-vivo from components, and methods for attaching and securing the individual components.

FIG. 1 shows a limb component 80 that is one aspect of the present invention. The limb component has a proximal end 81 with a proximal stent 84, a distal end 82 with a distal stent 85, and graft material 83. The proximal stent 84 is located internal to the graft material and is self-expanding with a series of caudal hooks or barbs 86 which puncture the graft material of the main body limb portion 33 when the stent 84 is deployed. The proximal stent 84 is designed to be attached to a limb support portion 33, 34 of the main body component 30 of a bifurcated endovascular graft. The distal stent 85 is also self-expanding and is designed to be attached to the vessel wall to anchor the distal end 82 of the limb component 80. Although shown external to the graft material with a series of caudal hooks or barbs 86, the distal stent 85 can be located internal to the graft material and may be of any type known within the art. Note that the hooks or barbs 86 at the proximal end 81 are angled in the distal direction, which is the direction of blood flow in the vessel. This angling helps to ensure better attachment of the limb component 80 to the main body component 30. The barbs on the distal end 82 of the limb point opposite to the blood flow. When the limb component 80 is compressed for delivery, the hooks or barbs 86 of the stents 84, 85 are also at least partially compressed.

FIG. 2 depicts an alternate embodiment of the limb component 80 shown in FIG. 1. The limb component 180 has relief holes 87 that are spaced around the circumference of the proximal end 81 of the graft material 183 to correspond to the hooks or barbs 86. The proximal stent 84 is attached to the graft material 183 using sutures 88 such that the hooks or barbs 86 protrude through the holes 87 when the limb component 180 is compressed for delivery, thereby preventing the compressed hook or barb 86 from tearing the graft material 183. It is contemplated that relief holes 87 may also be utilized for an internal stent 85 near the distal end 82 of the limb component 180 or whenever is desired to prevent tearing of the graft material by a compressed stent having hooks or barbs.

In a preferred embodiment, the limb component 80 proximal stent 84 is cut from a Nitinol tube using a laser beam and has five hooks 86 equally spaced around its circumference at 72 degrees apart. The stent 84 is heat-set for its final expanded diameter using a process known in the art, with the hooks 86 set at an approximately 45 degree angle using a inner mandrel and outer cylindrical tube, the stent 84 "electro polished", and the hooks 86 sharpened. The stent 84 is sutured inside the limb component 80 graft material 83 which has five holes 87 equally-spaced around its circumference. The holes 87, pre-punctured using a hot pin to melt the graft material 83, or ultrasonically punched, allow the five stent hooks 86 to protrude through the graft material 83 when the limb component 80 is compressed for delivery. When the limb component 80 is deployed within the limb support portion 33, 34 of a main body component 30, the stent 84 will expand, thereby causing the hooks 86 to penetrate the graft material of the main body component 30, forming a seal and anchoring the limb component 80 within the main body component 30. A balloon can also be used to set the hooks. A "tug" in the distal direction can also set the hooks.

Figure 3:
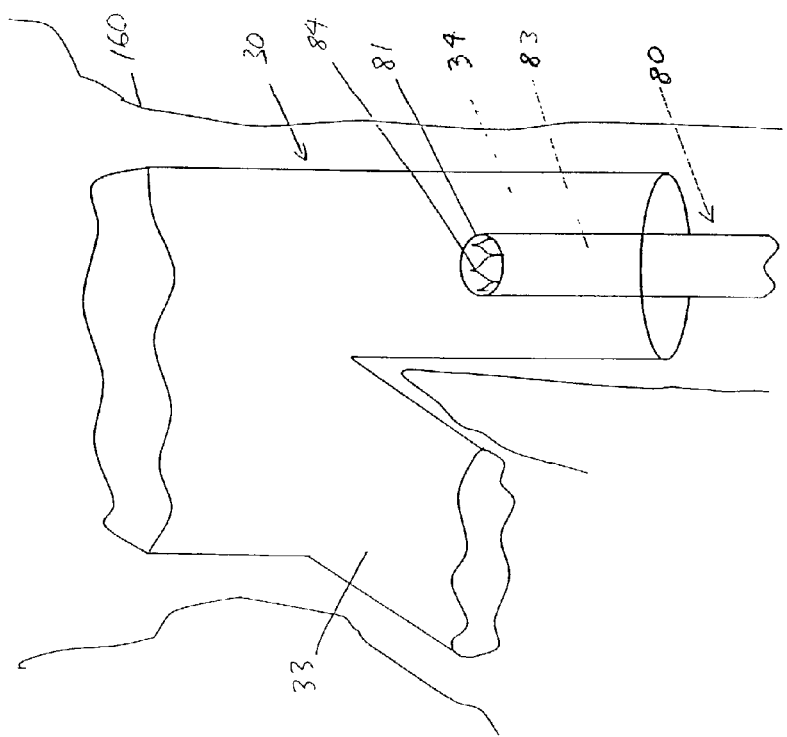
FIG. 3 is a side elevation, partial cross-sectional view of a main body component already implanted at the treatment site with the limb support portions floating freely and the limb component depicted in FIG. 1 inserted in a compressed state inside one of the limb support portions.

Referring to FIGS. 3 and 4, the method for joining the limb component 80 to the main body component 30 is shown. With the main body component 30 already implanted within the patient's vasculature 160, the limb component 80 is inserted in its compressed state within one of the limb support portions 34 of the main body component 30. The hooks or barbs 86 penetrate the limb graft before it is compressed. Once the limb component 80 is positioned properly, it is deployed. When the proximal end 81 of the limb component 80 is deployed, the radial force of the proximal stent 84 causes the hooks or barbs 86 to penetrate the graft material of the main body component 30 limb support portion 34, thereby locking the two components together and forming a seal between two layers of graft material. This graft-to-graft seal resists blood leakage better than the traditional stent-to-graft seal. The direction of blood flow (shown by arrow in FIG. 4) strengthens the seal by forcing the limb component 80 in the distal direction, thereby imbedding the hooks or barbs 86 in the graft material.

Furthermore, there is no pre-determined attachment point within the limb support portion 34 of the main body component 30. Therefore, the technician can position the proximal end 81 of the limb component 80 anywhere within the limb support portion 34, thereby allowing him to adjust the length of the limb component 80 between the main body component 30 limb support portion 34 distal end and the limb component 80 distal end 82 attachment point within the iliac "landing zone."

Moreover, several limbs 80 can be "chained" together, allowing the technician to customize the length of the limb section to the vasculature of individual patients or to correct for misjudgment of the length between the main body component 30 and the iliac "landing zone." It is contemplated that the graft material of the main body component 30 and limb component 80 can be polyethylene terephthalate (e.g. Dacron®) or PTFE (e.g. Teflon®) or any other similar material known in the art. It is further contemplated that the limb component 80 stent 84, 85 material can be Nitinol, Elgiloy, stainless steel, or any similar material known in the art that is either self-expanding or balloon expandable.

FIG. 5 depicts another alternate embodiment of the limb component 80 shown in FIG. 1. The limb component 380 has an external proximal stent 184 with hooks or barbs 86. The proximal stent 184 is covered by the limb component 380 graft material 83 which is folded over from a point proximal the stent 184 and attached to itself at a point distal the stent 184, thereby forming an inner graft portion 90 and outer graft portion 91 at the proximal end 81 of the limb component 380. Hooks or barbs 86 on the proximal stent 184 protrude through the outer graft portion 91. When the limb component 380 is deployed, the hooks or barbs 86 penetrate the graft material of the main body component 30 limb support portion 33, 34, thereby forming a mechanical interconnection between them. Although the mechanical interconnection is between the hook or barbs 86 of the limb component 380 and graft material of the limb support portion 33, 34, the graft-to-graft contact between the outer graft portion 91 of the limb component 380 and the graft material of the limb support portion 33, 34 provides a better seal against blood leakage between the components than proximal stent 184-to-graft contact would.

Figure 6:
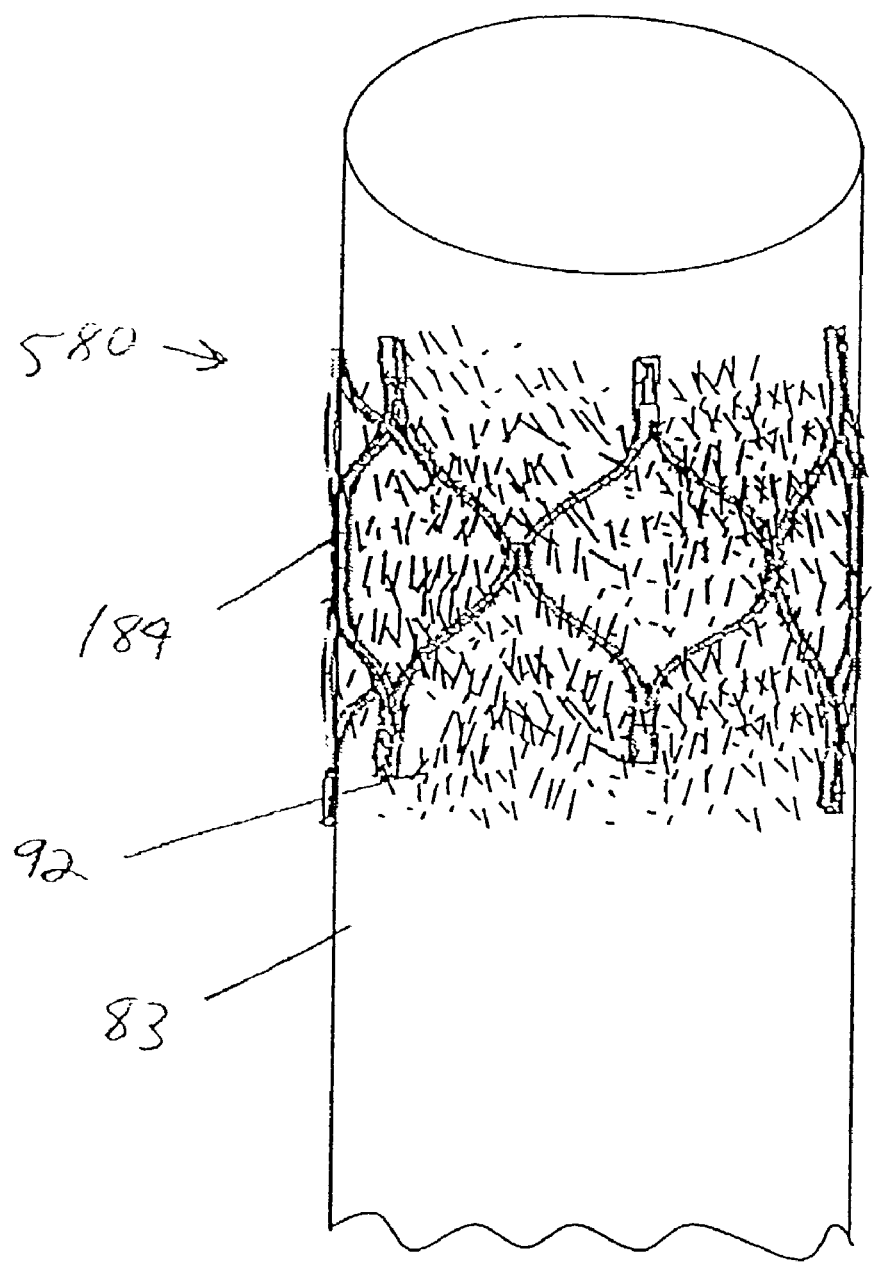
FIG. 6 is a partial perspective view depicting a traditional embodiment of the main body and limb components with fuzzy yarns attached to the internal limb attachment stent of the limb support portion and the external limb attachment stent of the limb component, the graft material partially removed to show the tufting of the limb support portion internal stent.

It is contemplated that tufting 92 can also be used where the seal between the limb component and main body component is achieved by traditional methods. For example, FIG. 6 depicts a limb component 580 with an external proximal stent 184 that is deployed within the limb support portion 134 of a main body component 130 with an internal distal stent 52. The seal is formed by the main body component 130 internal distal stent 52 that resists the expansion of the limb component 580 external proximal stent 184. Tufting 92 on the outside of the limb component 580 graft material 83 protrudes through the external proximal stent 184. Likewise, tufting 92 on the inside of the limb support portion 134 graft material protrudes through the internal distal stent 52. The tufting 92 fills spaces between the stents 52, 184 and graft material as well as spaces between the two stents 52, 184, thereby promoting blood clotting, improving the seals, and reducing blood leakage. The location of the stents 52, 184 in FIG. 6 is intended for demonstration purposes only as it is contemplated that tufting 92 may be used to improve the seal anytime stents are used.

Figure 7:
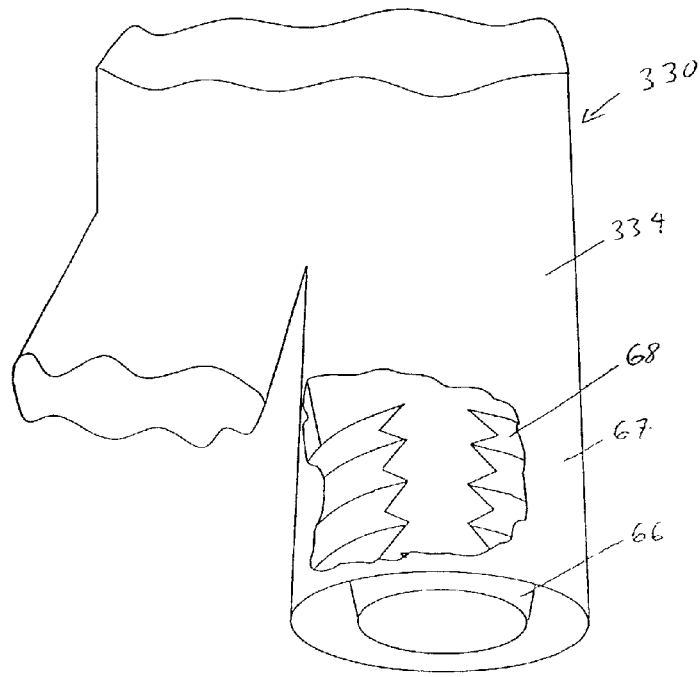
FIG. 7 is a partial perspective view of an alternate embodiment of the main body and limb components of the present invention with the main body component limb support portion having a tapered inner layer and internal sealing material and the limb component having an internal support stent and external sealing material, the graft material and sealing material partially removed to show the limb support portion internal taper and limb component internal stent.
Figure 8:
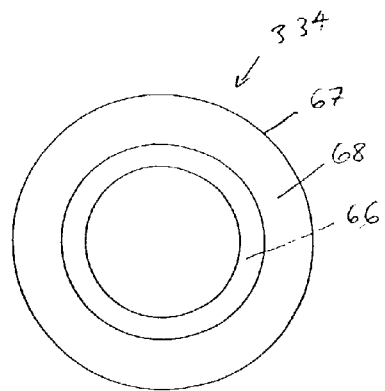
FIG. 8 is a view of the main body component limb support portion depicted in FIG. 7 from the distal end.
Figure 9:
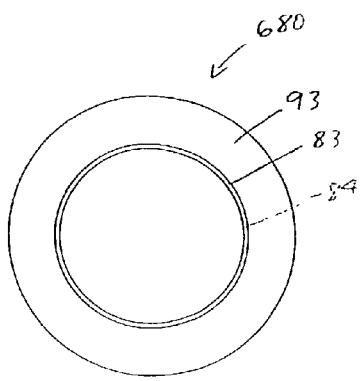
FIG. 9 is a view of the limb component depicted in FIG. 7 from the proximal end.

Alternately, the components may be attached without hooks or barbs which can lead to deterioration or tearing of the graft material. FIGS. 7-9 depict one such method. The main body component 330 is defined by a limb support portion 334 that has a tapered inner graft layer 66 and an outer graft layer 67. The outer graft layer 67, which parallels the profile of the main body component 330, is further defined by a sealing material 68 around the inner circumference. The sealing material 68, which may be formed of graft material or plastic, forms a pattern such as a saw-tooth pattern. The tapered inner graft layer 66 is attached to the inner circumference of the outer graft layer 67 proximal the sealing material 68, thereby creating a funnel for blood flow into the attached limb component 680. The limb component 680 has a self-expanding internal stent 84 at its proximal end 81. The limb component 680 is further defined by a sealing material 93 that is secured external the graft material 83. The sealing material 93 is similar to that on the limb support portion 334, but with an inverse pattern.

Figure 10B:
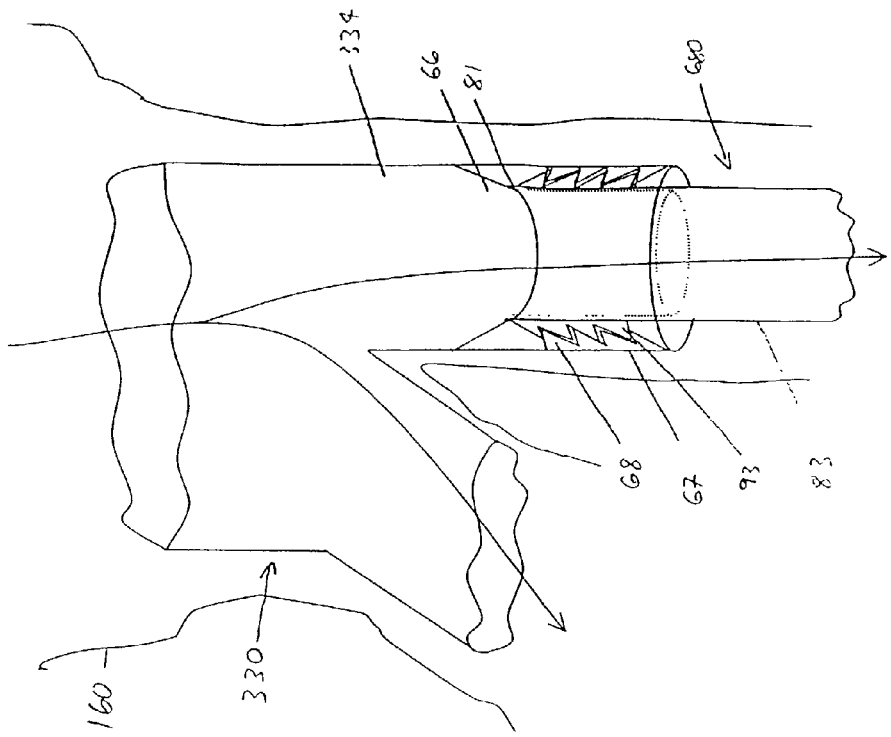
FIG. 10B is a side elevation, partial cross-sectional view a main body component depicted in FIG. 7 already implanted at the treatment site with the limb support portions floating freely and the limb component depicted in FIG. 7 deployed inside one of the limb support portions.
Figure 10A:
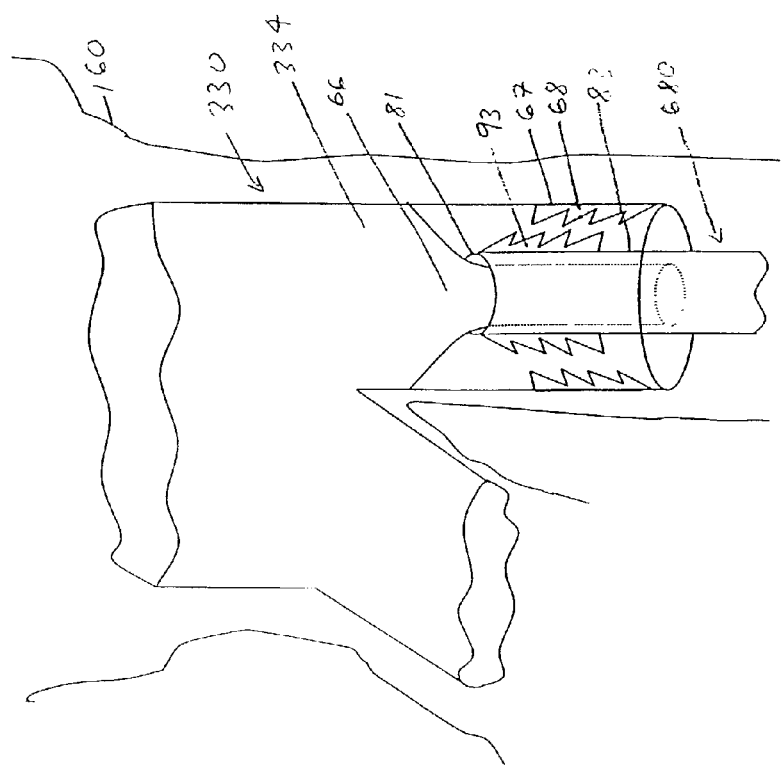
FIG. 10A is a side elevation, partial cross-sectional view of a main body component depicted in FIG. 7 already implanted at the treatment site with the limb support portions floating freely and the limb component depicted in FIG. 7 inserted in a compressed state inside one of the limb support portions.

FIGS. 10A and 10B depict the joint formed between the main body component 330 and limb component 680 using this method. The main body component 330 is deployed first in the patient's vasculature. The flow of blood (indicated by the arrow) helps to keep the tapered inner layer 66 of the limb support portion 334 open. The limb component 680 is inserted and partially deployed within the outer graft layer 67 of the limb support portion 334 such that the inner layer 66 of the limb support portion 334 is inside the limb component 680, but the sealing material 93 of the limb component 680 does not engage the sealing material 68 of the limb support portion 334. The partially-deployed limb component 680 is moved distally such that the edges of its sealing material 93 pattern are slightly distal the corresponding edges of the limb support portion 334 sealing material 68 pattern and the limb component 680 is then fully deployed. The flow of blood (shown by the arrow) forces the inner layer 66 of the limb support portion 334 to expand and thereby causes the limb component 680 to advance distally. The radial expansion of the limb component 680 proximal stent 84 causes the limb component 680 sealing material 93 to engage the limb support portion 334 sealing material 68, thereby preventing further distal migration of the limb component 680. The resulting mechanical joint between the limb component 680 and limb support portion 334 sealing materials 93, 68 provides better resistance to distal migration of the limb component 680 than traditional methods, such as a frictional joint, without deterioration or tearing of the graft material 83. It is contemplated that this method may be used to join any two components where the first-deployed component has a tapered inner graft layer and an outer graft layer with sealing material on its inner surface and the second component, with an internal self-expanding stent and sealing material external the graft material, is deployed within the first component such that the first component tapered inner layer is inside the second component.

Figure 11B:
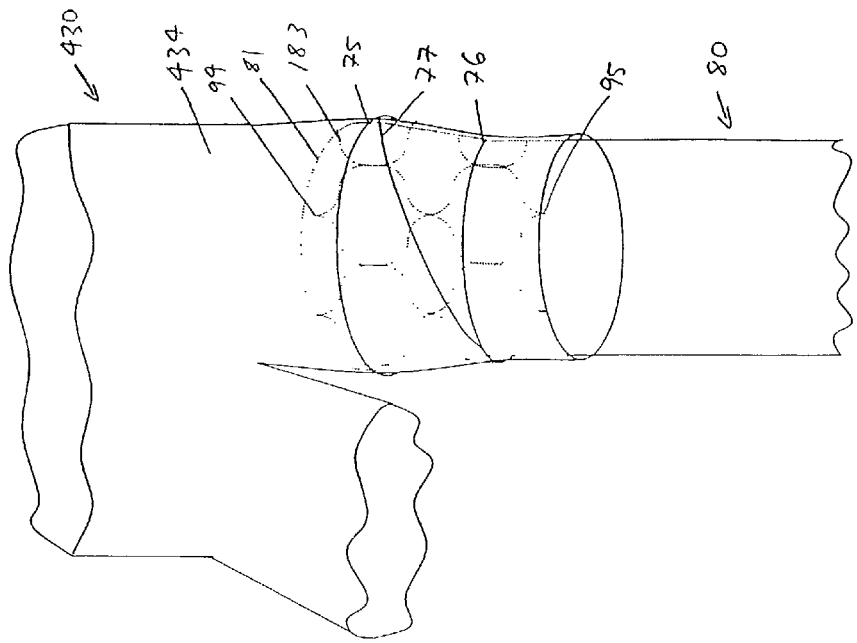
FIG. 11B is a partial perspective view depicting the joint formed when the limb component shown in FIG. 11A is deployed within the limb support portion of the main body component shown in FIG. 11A.
Figure 11A:
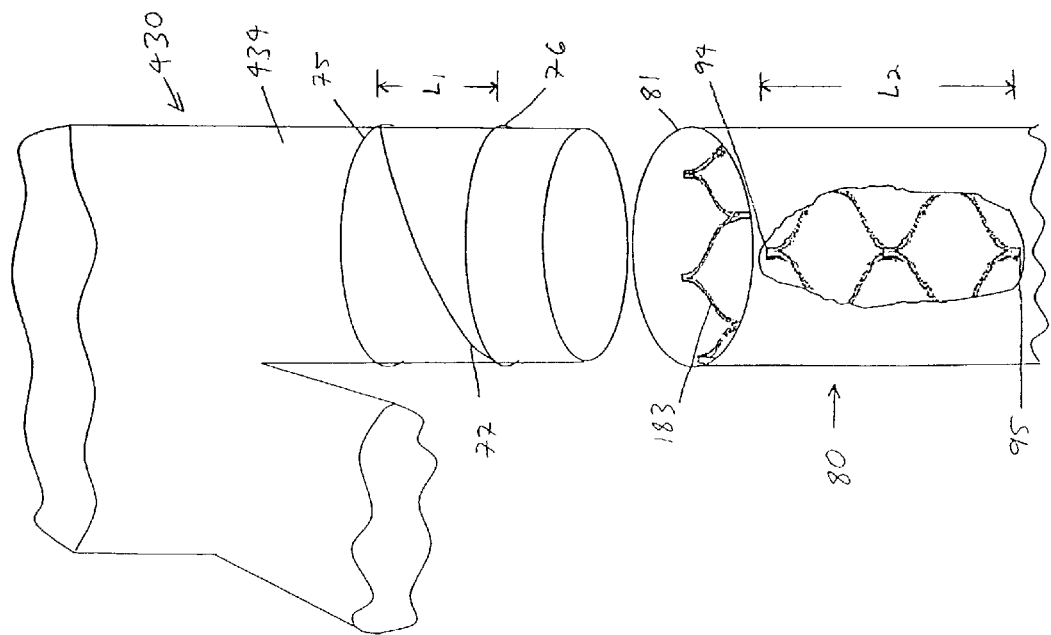
FIG. 11A is a partial perspective view of an alternate embodiment of the main body and limb components of the present invention where the limb support portion of the main body component has a "lasso" attached to the distal end and the limb component has an internal support stent.

An alternative method of attaching components without hooks or barbs is depicted in FIGS. 11A and 11B. The main body component 430 is defined by a limb support portion 434 which has a "lasso". The "lasso" has a proximal loop 75, a distal loop 76, and a transition portion 77. The "lasso" may be formed by two slipknots attached or laced through the graft material and connected by a thread or a single thread that is laced through the graft material and attached at both ends such that the loops cannot move along the axis of the graft. The "lasso" is further defined by a length (indicated as $L_1$ In FIG. 11A). Wire, suture material, ribbon, rope, or string may be used instead of thread. The limb component 80 is defined by a self-expanding internal stent 183 at the proximal end 81. The proximal stent 183 is further defined by a proximal end 94, a distal end 95, and an axial length (indicated as $L_2$ in FIG. 11A). The total length of the material used to create the two "lasso" loops minus the transition length is less than twice the circumference of the expanded limb component 80 such that expanding one of the loops causes the other loop to constrict to a diameter less than that of the limb component 80. However, the total length of the material used to create the two "lasso" loops and transition portion must be sufficient to preclude the expansion of one loop from causing the other loop to constrict so much that it occludes the limb component 80. Furthermore, the length of the "lasso" is less than the axial length of the limb component 80 proximal stent 183 ($L_1<L_2$) such that the limb component 80 may be positioned and the "lasso" proximal loop 75 expanded by the deployed stent 183 proximal end 94 while the "lasso" distal loop 76 constricts around the stent 183 distal end 95.

FIG. 11B depicts the joint formed between the main body component 430 and limb component 80 using this method. The main body component 430 is deployed first. The limb component 80 is delivered in a compressed state and positioned such that the limb support portion 434 proximal loop 75 is directly above the proximal end 94 of the limb component proximal stent 183 and the limb support portion distal loop 76 is directly above the distal end 95 of the limb component proximal stent. When the limb component 80 proximal stent 183 is deployed, the radial force of the proximal end 94 causes the limb support portion 434 proximal loop 75 to expand, thereby causing the limb support portion 434 distal loop 76 to contract around the distal end 95 of the stent 183. The resulting joint between the components is both mechanical, between the radial force of the distal end 95 of the stent 183 and the constricted distal loop 76, and frictional, between the limb component 80 and limb support component 434 graft materials. Such a joint provides better resistance to distal migration of the limb component 80 than traditional methods, such as an entirely frictional joint, without deterioration or tearing of the graft material. It is contemplated that this method may be used to join any two components where the first-deployed component has a "lasso" mechanism at the distal end and the second component, with a proximal support stent, is deployed within the first component such that the proximal end of the "lasso" is expanded by the stent while the distal end of the "lasso" constricts around the stent. Also, the entire stent could be placed above the distal loop. Although FIGS. 11A and 11B depict an internal limb component proximal stent 183, it is contemplated that the stent may be located external the limb component graft material.

Another alternative method of attaching components without hooks or barbs is depicted in FIGS. 12A and 12B. The main body component 530 is defined by a limb support portion 534 that has a tapered middle portion 78 and a "bell-bottom" distal portion 70. The limb support portion 534 is further defined by an external support stent 152 located proximal the tapered portion 78 and an external "bell-bottom" stent 171. The limb component 80 is defined by a self-expanding internal stent 183 at its proximal end 81.

In a preferred embodiment, the contra-lateral limb support portion 534 has a tapered middle portion 78 and "bell-bottom" distal portion 70. The contra-lateral limb support portion 534 external stent 152 has an axial length of 1 centimeter and the "bell-bottom" portion 70 has an axial length of 2 centimeters with a 0.75 centimeter "bell-bottom" stent 171 at the distal end. Furthermore, the ipsi-lateral limb support portion 533 has an external stent (not shown) with an axial length of 1 to 2 centimeters just proximal a tapered distal end (not shown). Moreover, the contra-lateral limb support portion 534 is at least 1.5 centimeters longer than the ipsi-lateral limb support portion 533, thereby allowing packing of the main body component 530 without any stents occupying the same axial space. The limb component 80 internal proximal stent 183 has an axial length of 1 to 2 cm. All stents are made of Nitinol.

FIG. 12B depicts the joint formed between the main body component 530 and limb component 80 using this method. The main body component 530 is deployed first. The flow of blood (indicated by the arrow) and the limb support portion 534 stents 152, 70 keep a passageway open through which the limb component 80 is inserted. The limb component 80 is delivered in a compressed state and inserted into the limb support portion 534 such that the distal end of the limb component 80 proximal stent 183 is proximal to the limb support portion 534 tapered middle portion 78. When the limb component 80 is deployed, the radial force of the proximal stent 183 forces the limb component 80 graft material 83 against the limb support portion 534 graft material and the tapered portion 78 prevents distal migration of the limb component 80. The resulting joint between the components is both mechanical, between the expanded stent 183 and tapered portion 78, and frictional, between the limb component 80 and limb support component 534 graft materials. Such a joint provides better resistance to distal migration of the limb component 80 than traditional methods, such as an entirely frictional joint, without deterioration or tearing of the graft material. It is contemplated that this method may be used to join any two components where the first-deployed component has a tapered middle portion and "bell-bottom" distal end and the second component, with a proximal support stent, is deployed within the first component such that the distal end of the stent is proximal to the tapered portion. Although FIGS. 12A and 12B depict external limb support portion stents 152, 171 and an internal limb component proximal stent 183, it is contemplated that the stents may be located either internal or external the graft material.

Figure 13:
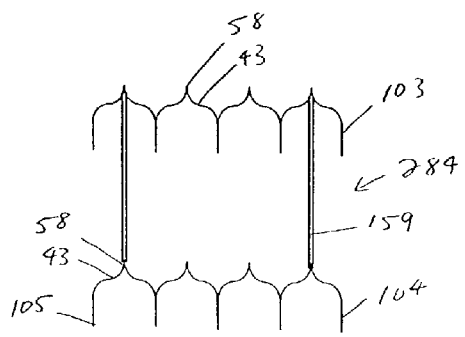
FIG. 13 is a schematic view of an alternate stent design of the present invention in which separate proximal and distal cell portions are connected by cell connectors between the wishbone areas of the struts of the proximal and distal cell portions.

An alternative method, known within the art, of attaching components without hooks or barbs is engaging a stent attached external the proximal end of the limb component with a main body component limb support portion having an internal cuff or loops sewn inside the graft material near the distal end. Utilizing the stent shown in FIG. 13 facilitates easier mating of the limb component and limb support portion of the main body component. The stent 284 is defined by cells with separate proximal 103 and distal 104 portions having cell connectors 159 between some of the proximal wishbone areas 58 of the cells. The cell connectors are longer than the compressed length of the proximal cell portions. Therefore, it is possible to partially deploy the proximal portions of the cell while maintaining control of the distal portion of the cell and cell connectors, a process which produces an "umbrella" effect.

Figure 14A:
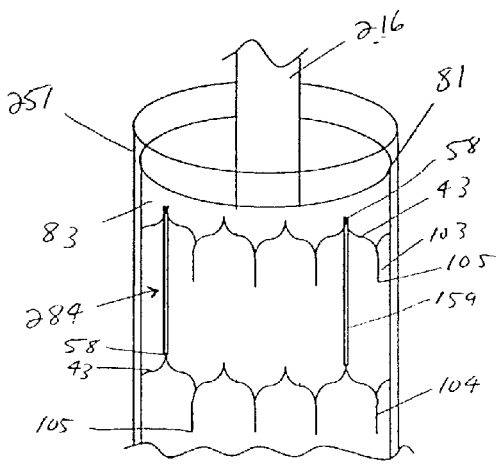
FIG. 14A is a partial perspective view depicting the proximal end of a limb component of the present invention with an internal proximal stent utilizing the alternate stent design shown in FIG. 13 and held in a compressed state by a sheath that is shown as transparent.
Figure 14B:
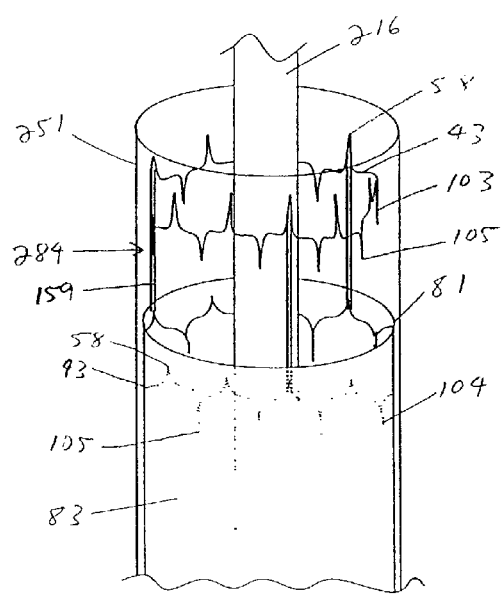
FIG. 14B is a partial perspective view depicting the proximal end of a limb component of the present invention with an external proximal stent utilizing the alternate stent design shown in FIG. 13 and held in a compressed state by a sheath that is shown as transparent.
Figure 14C:
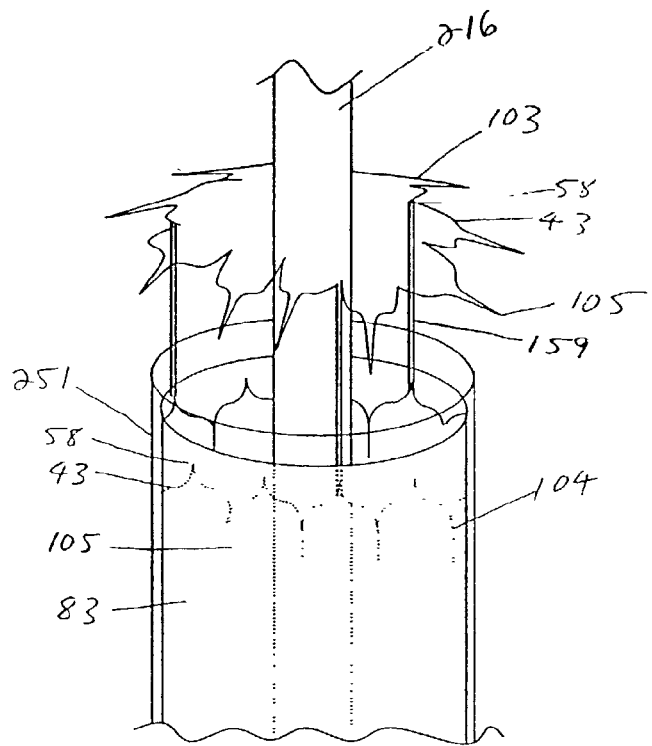
FIG. 14C is a partial perspective view depicting the "umbrella" or grappling pattern produced when the sheath in FIG. 14A is retracted distally to expose the upper cell portions of the stent.

The stent may be located external the limb component graft material 83, as shown in FIG. 14A, or the distal cell portions 104 may be located internal the graft material with the proximal cell portions 103 located beyond the proximal end 81 of the limb, as shown in FIG. 14B. When the proximal cell portion of the stent is uncovered but the distal cell portion of the stent is still covered, as shown in FIG. 14C, the proximal cell portion starts to deploy. Since the distal end of the cell connectors 159 are still covered by the catheter jacket 251 and restrain the proximal wishbone area 58 of the proximal cell portions, the deployment is only partial and an "umbrella" or grappling hook shape results. By maneuvering the catheter inner member 216, the distal wishbone area 105 of the partially deployed proximal cell portion 103 may be mated with a cuff or other attachment mechanism (not shown) of a limb support portion of the main body component. Once proper engagement of the limb component and limb support portion is verified, either visually seeing the limb support component move or feeling a tug once the distal wishbone area 105 engages the attachment mechanism, the catheter jacket 251 is retracted distally to fully deploy the proximal 103 and distal 104 cells portions of the stent.

It is contemplated that the "umbrella" stent 284 may be permanently attached to a catheter and utilized as a snare to retrieve clots or pieces of medical devices such as coils, catheter tips, or guidewires. It is also contemplated that an umbrella stent 284 having sharpened distal wishbone areas 105 may be utilized to anchor a graft to the walls of a vessel.

Figure 15:
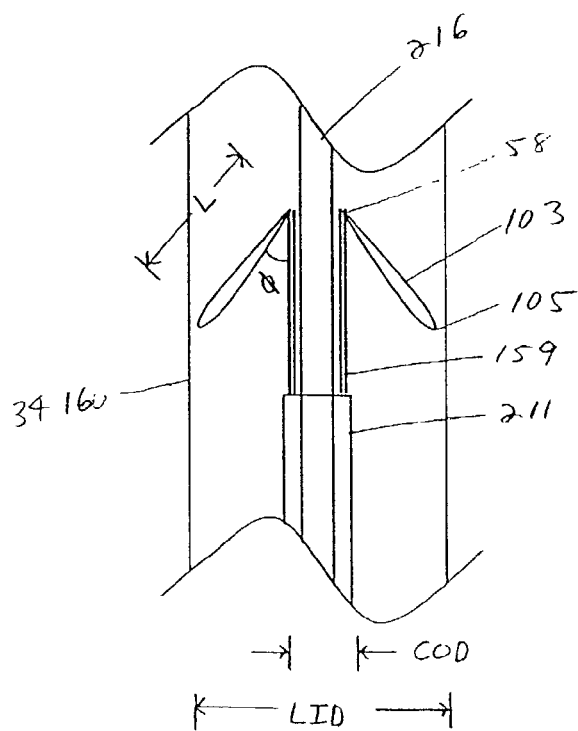
FIG. 15 is a schematic partial cross-sectional view of the upper cell portions of the stent utilizing the alternate stent design shown in FIG. 13 which is partially deployed and indicating pertinent dimensions.

The minimum length of the proximal cell portions (indicated as L in FIG. 15) is a function of the catheter inner member 216 outer diameter (indicated as COD in FIG. 15), the limb support portion 34 or lumen 160 inner diameter (indicated as LID in FIG. 15), and angle at which the cell portions expand (indicated as φ in FIG. 15). The relationship is shown by the formula:

$$\Delta D = LID - COD$$

$$L = (\Delta D/2)/\sin \phi$$

In order to provide the grappling effect in both axis, at least 3 cell connectors are provided. Although the figures show 3 cells between cell connectors, it is contemplated that there may be any number of cells between cell connectors. It is further contemplated that any cell pattern and size, as well as cells with sharp or smooth lower wishbone portions 105 may be used as long as adequate expansion is achieved and the attachment site is adequate to accommodate the cells.

Whether the limb attachment methods of the present invention or methods known within the art are utilized, the manner in which the stents are attached to the graft material may effect the strength or fluid seal of the joint between the limb support portion and limb component. By providing additional graft material in areas where the stent-to-graft attachment is prone to leaks or wear as well as enabling the attached stent to move relative to the graft material may result in a better joint.

FIGS. 16A and 16B show a limb component 780 with a self-expanding internal proximal stent 84 attached to the proximal end 81 of the graft material 83 with sutures 88 at only the most proximal and most distal ends of the stent such that an additional layer of graft material is formed where the stent has its widest opening between struts. This is the area most susceptible to the "parachute" effect caused when blood leaks between the joint formed between a proximal limb stent and main body component limb support portion distal stent, whereby the blood collects in the largest graft-to-graft area in the frame stent openings and fills like a parachute. The additional graft material in this area resists the tendency of blood to collect. The additional area of graft material may be formed by attaching the most proximal or most distal end of the stent to the graft material with sutures and pulling the graft material outside itself to form an overlapping area 100 before attaching the other end of the stent to the graft material, thereby forming a fold of graft material around the circumference of the graft material which traverses the widest area between stent struts. It is contemplated that an additional area of graft material may also be utilized for the main body component limb support portion distal stent or for any type of vessel repair the requires an implant seal.

Providing a graft pocket within which a self-expanding external stent without attachment hooks or barbs may move is one way to facilitate a better joint between the limb support portion of the main body component and the limb component. The stent, which is not attached to the graft material, moves proximally or distally within the pocket, thereby facilitating self-alignment after deployment. The ability to self-align provides a more secure joint. It is contemplated that a graft pocket may be used for a main body component limb support portion distal stent, limb component proximal stent, or whenever it is desired to attach a self-expanding stent or frame to a graft type material for human vessel repair.

A graft pocket may be formed by attaching additional graft material. FIGS. 17A and 17B show a limb component 880 with a self-expanding external proximal stent 184 and an additional graft ring patch 249 attached to the proximal end 81 of the graft material 83, thereby covering the external stent. The graft ring patch, which is attached by sutures 88 at its proximal and distal extremities, forms a pocket within which the stent may move. It is contemplated that the graft ring patch may be attached with a continuous stitching pattern around the entire circumference of the graft, rivets or other methods known within the art rather than with individual sutures. It is also contemplated that a graft ring patch may be attached to the distal end of the main body component limb support portion.

Figure 18A:
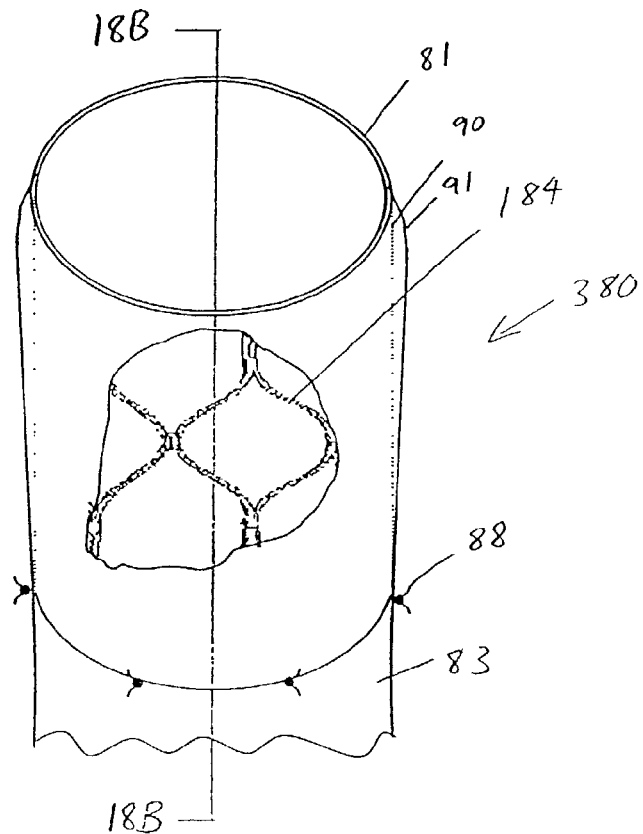
FIG. 18A is a partial perspective view depicting the proximal end of a limb component of the present invention where the graft material is folded over an unattached external stent and the graft material is partially removed to show the stent.
Figure 18B:
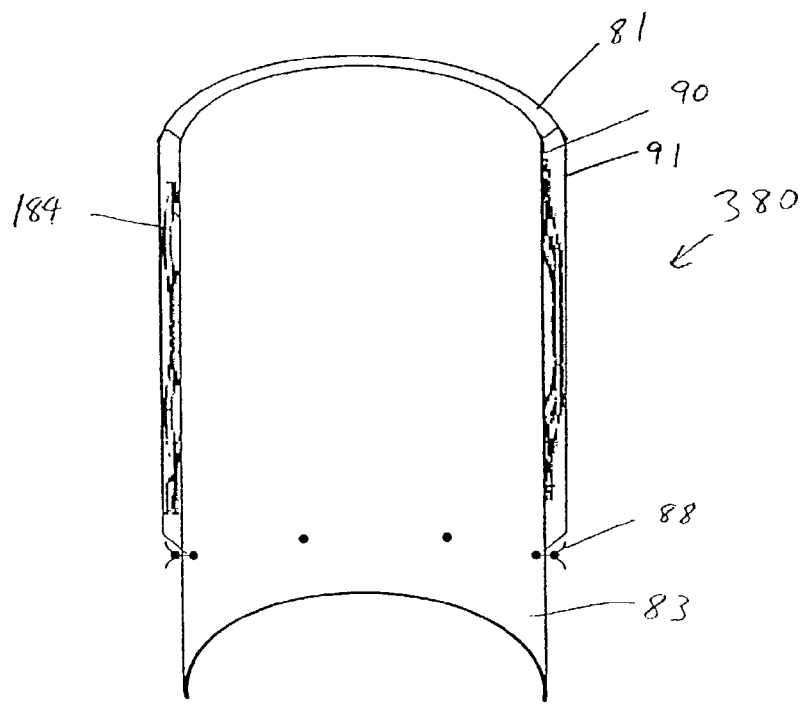
FIG. 18B is a cross-sectional view along line 18B-18B of FIG. 18A.

Alternately, a graft pocket may be formed without attaching additional graft material. FIGS. 18A and 18B show a pocket formed by pulling the proximal end of the limb component 380 graft material 83 distally over the external self-expanding proximal stent 184 and attaching it to the graft material distal the stent. In a preferred process, the proximal stent is covered by the limb component graft material, thereby forming a pocket between an inner graft portion 90 and outer graft portion 91 at the proximal end 81 of the limb component. Attachment of the graft material distal the enclosed stent may be by sutures 88, a continuous stitch around the graft, rivets or other methods known within the art. It is also contemplated that the graft fold-over may be used at the distal end of the main body component limb support portion.

Instead of providing a graft pocket, additional strips of graft material attached to the external surface of the graft material may be utilized to facilitate stent self-alignment without completely enclosing the stent in graft material. It is contemplated that additional strips of graft material that hold self-expanding stents in place may be utilized whether or not the stent has attachment hooks or barbs. It is also contemplated that additional strips of graft material may be used for a main body component limb support portion distal stent, limb component proximal stent, or whenever it is desired to attach a self-expanding stent or frame to a graft type material for human vessel repair.

As shown in FIGS. 19A, 19B and 19C, a single strip of graft material may be used with a stent having no attachment hooks or barbs. The limb component 980 with a self-expanding external proximal stent 184 is held in place by a strip of graft material 101 that traverses the circumference of the proximal end 81 of the graft material 83. The strip of graft material 101, which is attached by sutures 88 such that loops 102 are formed within which the stent struts may move, may be thicker or thinner than the limb component graft material 83. It is contemplated that the strip of graft material 101 may also be attached by rivets or other methods known within the art.

Figure 20A:
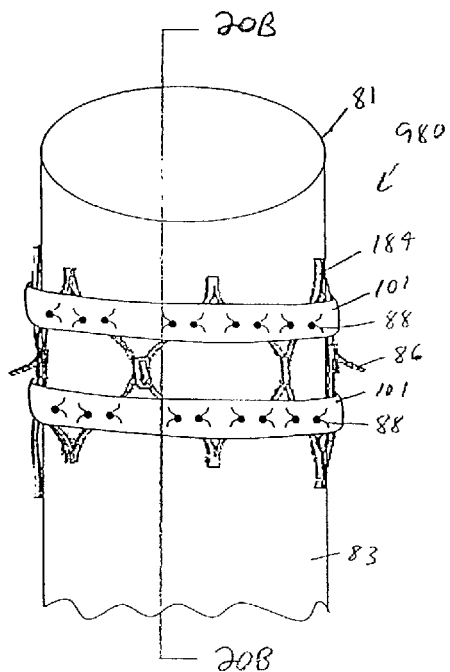
FIG. 20A is a partial perspective view depicting the proximal end of a limb component of the present invention where two graft belts are attached over an external stent having attachment hooks or barbs.
Figure 20B:
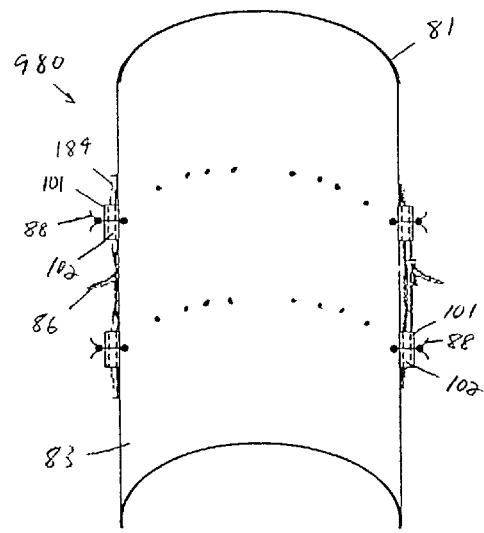
FIG. 20B is a cross-sectional view along line 20B-20B of FIG. 20A.
Figure 20C:
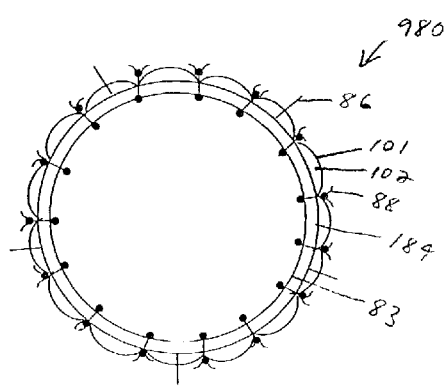
FIG. 20C is a view of the limb component depicted in FIG. 20A from the proximal end.

Alternately, two strips of graft material may be used with a stent having attachment hooks or barbs. FIGS. 20A, 20B and 20C show a limb component 980 with a self-expanding external proximal stent 184 having attachment hooks or barbs 86 and two strips of graft material 101 that traverse the circumference of the proximal end 81 of the graft material 83. The strips of graft material 101, which are attached by sutures 88 such that loops 102 are formed within which the stent struts may move, may be thicker or thinner than the limb component graft material 83. The strips of graft material 101 are attached above and below the attachment hooks or barbs 86, thereby precluding tangling.

Providing additional protection at the areas where stents or other metal contact graft material may decrease wear and increase reliability of endovascular graft components. Sites that are susceptible to wear, and hence would benefit from such protection, include frame attachment sites, areas where hooks or barbs penetrate the graft material, and areas of friction or motion between metal features and graft material.

One way to reinforce graft material sites susceptible to wear is to reinforce the graft fabric. A coating, such as a thin coat of a biocompatible elastomer can be screen printed or otherwise applied in a band around the graft.

Coating the entire surface of the graft material may be preferred, particularly if ultra thin woven PET graft material is used to reduce implant bulk. As the thickness of the graft material is reduced, the permeability increases. Coating the entire surface of the graft material not only increases reliability of the graft but also reduces permeability without increasing bulk. A polyurethane co-polymer coating may be dip-coated onto the woven PET substrate. When the solvent is removed, a biocompatible, non-thrombogenic surface to contact the arterial blood is left bonded to the PET material. The thickness of the coating may vary from a few to many microns. It is contemplated that multiple dipping and drying steps may be performed to produce a thicker coating to meet permeability requirements.

Alternately, the weave pattern of the graft material may be altered in certain regions to provide extra strength where needed. A rip stop type graft material weave is one example of a typical graft reinforcement method.

Figure 21A:
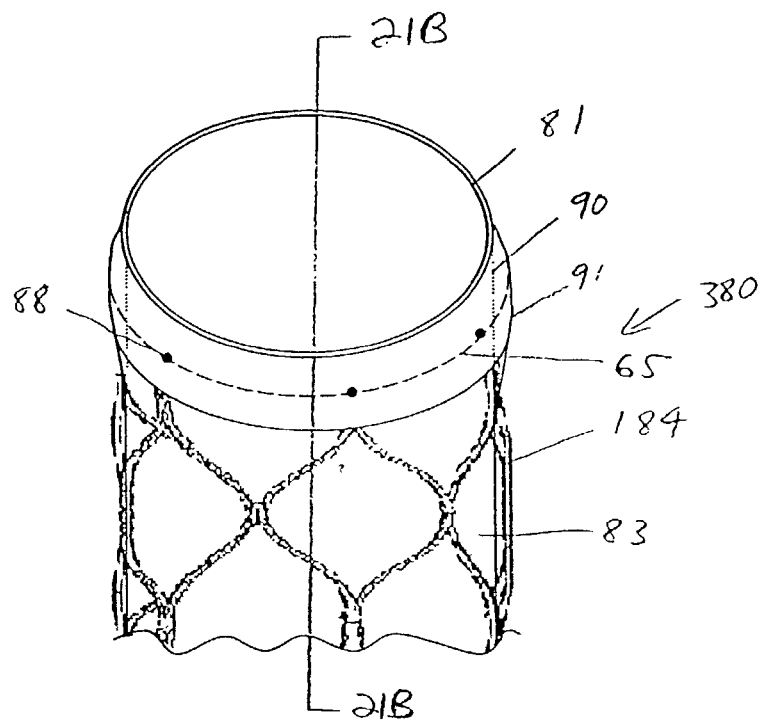
FIG. 21A is a partial perspective view depicting the proximal end of a limb component of the present invention where the graft material is folded over the connector eyelets of an external stent.
Figure 21B:
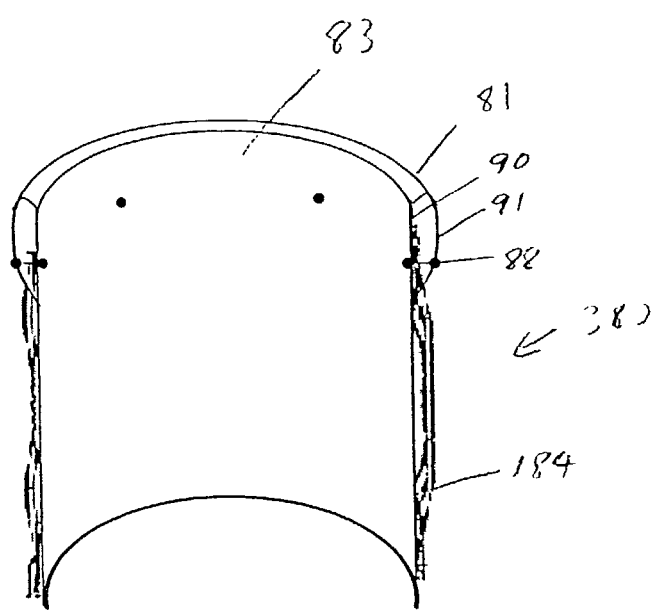
FIG. 21B is a cross-sectional view along line 21B-21B of FIG. 21A.

An alternate way to reinforce areas of the graft susceptible to wear is to provide an additional layer of graft material. FIGS. 21A and 21B show a limb component 380 with the graft material folded over to provide additional reinforcement for the site where a self-expanding external proximal stent 184 is attached to the graft material 83. In a process similar to that shown in FIGS. 18A and 18B, a pocket is formed between an inner graft portion 90 and outer graft portion 91 at the proximal end 81 of the limb component into which the proximal eyelets of the stent are placed. The stent is attached using sutures 88 which are sewn through the eyelets and the double layer of graft material, thereby increasing the durability of the joint. Additionally, a running stitch 65 similar to that defined for connection of the main body attachment stent may provide further reinforcement of the suture joint. It is contemplated that the graft fold-over may be used to attach an internal proximal stent by folding the graft material inside rather than outside the original graft material layer. It is further contemplated that the graft fold-over may be used to attach a stent to the distal end of the main body component limb support portion or whenever a stent is attached with sutures to graft material.

Although the various attachment mechanisms are depicted with respect to the contra-lateral limb component, it is to be noted that this is done for demonstration purposes only. It is contemplated that the attachment mechanisms depicted may be applied to attach the ipsi-lateral limb component of a bifurcated endovascular graft as well as to attach any two modular endovascular graft components. It is further contemplated that the various attachment mechanisms depicted herein may be swapped. For example, the attachment mechanism depicted as part of the limb component may be provided as part of the main body component and the attachment mechanism depicted as part of the main body component may be provided as part of the limb component.

Figure 22:
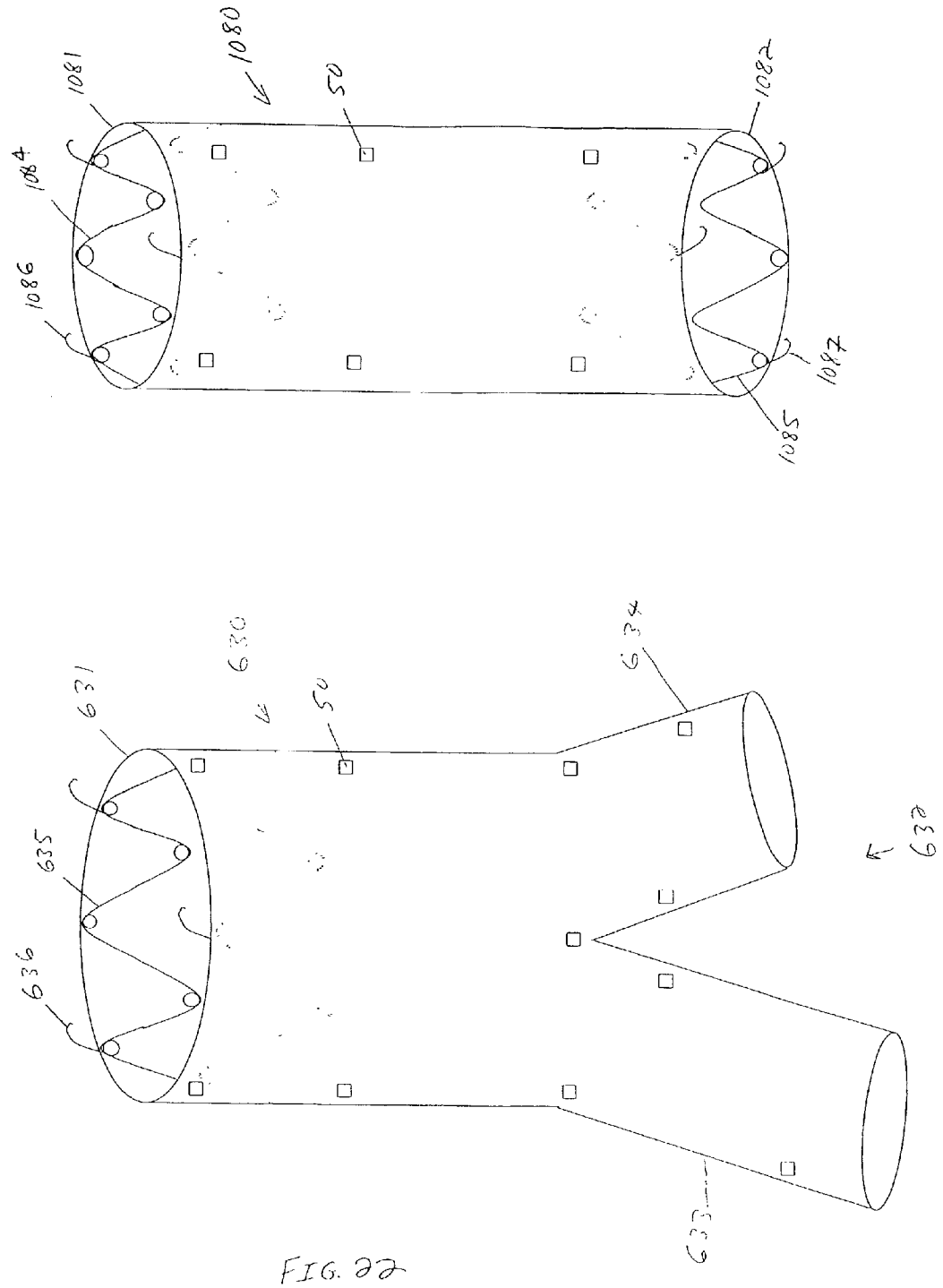
FIG. 22 is a perspective view, depicting a limb component and main body component of an alternate embodiment of the invention.

Referring to FIG. 22, another alternate embodiment of the invention is shown. The main body component 630 is defined by a proximal end 631 and distal end 632. The limb component 1080 is defined by a proximal end 1081 and distal end 1082.

The proximal end 631 of the main body component 630 has a frame 635 with caudal hooks or barbs 636 designed to be embedded in a vessel wall. The distal end 632 has two limb support portions 633, 634 designed to receive the proximal end 1081 of the limb component 1080. Radiopaque markers 50 may be attached to the graft material to facilitate placement of the main body component 630 in a body lumen. In a preferred embodiment, the frame 635 is sewn to the graft material and made of Elgiloy® with four V-hooks 636 spaced 90° apart around the circumference.

The proximal end 1081 of the limb component 1080 has a frame 1084 with caudal hooks or barbs 1086 designed to be attached to a limb support portion 633, 634 of the main body component 630. The distal end 1082 also has a frame 1085 with hooks or barbs 1087 designed to be embedded in a vessel wall. Radiopaque markers 50 may be attached to the graft material to facilitate placement in a body lumen. In a preferred embodiment, each frame 1084, 1086 is sewn to the graft material and made of Elgiloy® with three V-hooks 1086, 1087, respectively, spaced 120° apart around the circumference.

Figure 23A:
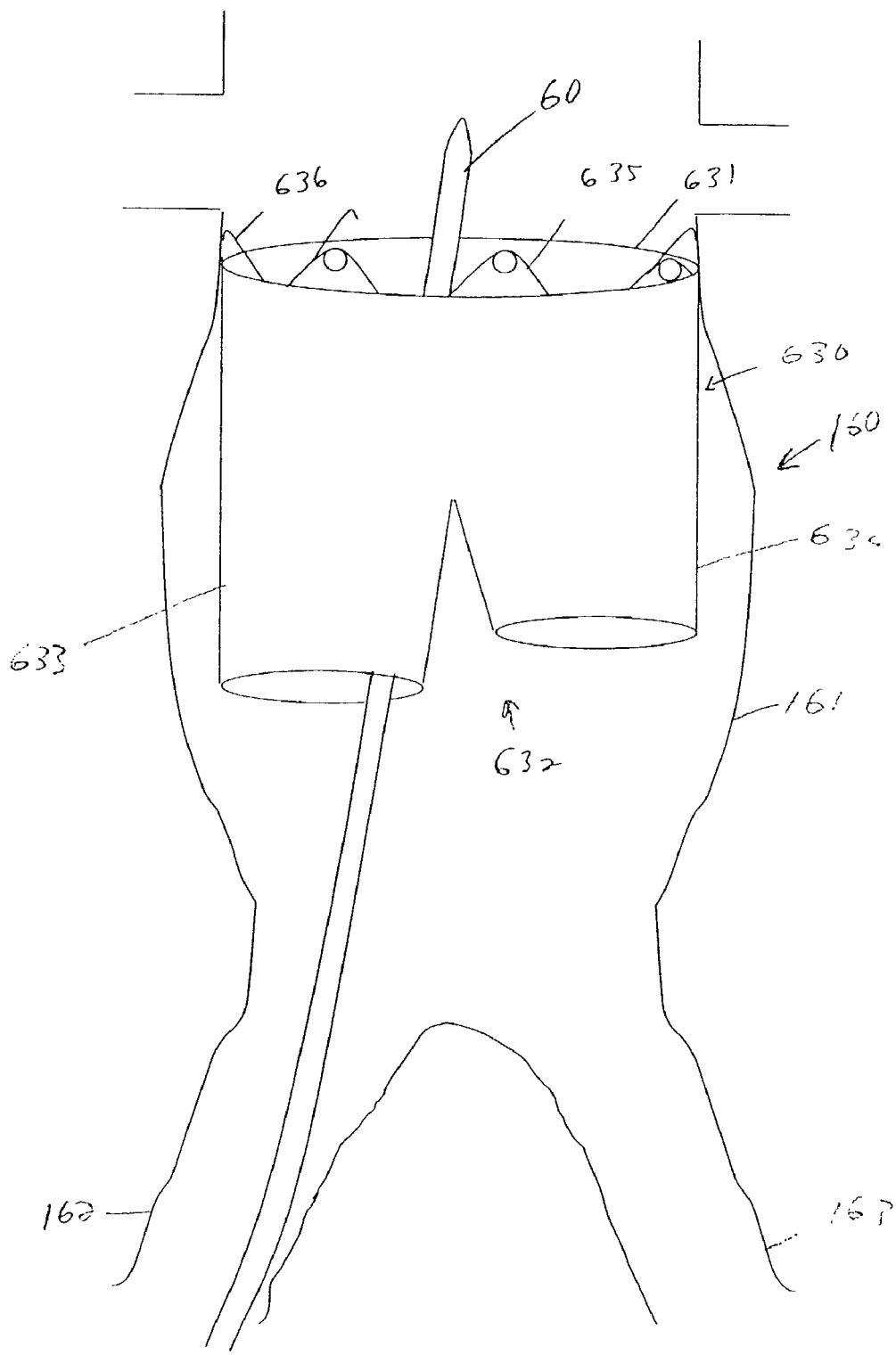
FIG. 23A is a side elevation, cross-sectional view of the main body component illustrated in FIG. 22 implanted at the treatment site with the limb support portions floating freely.
Figure 23B:
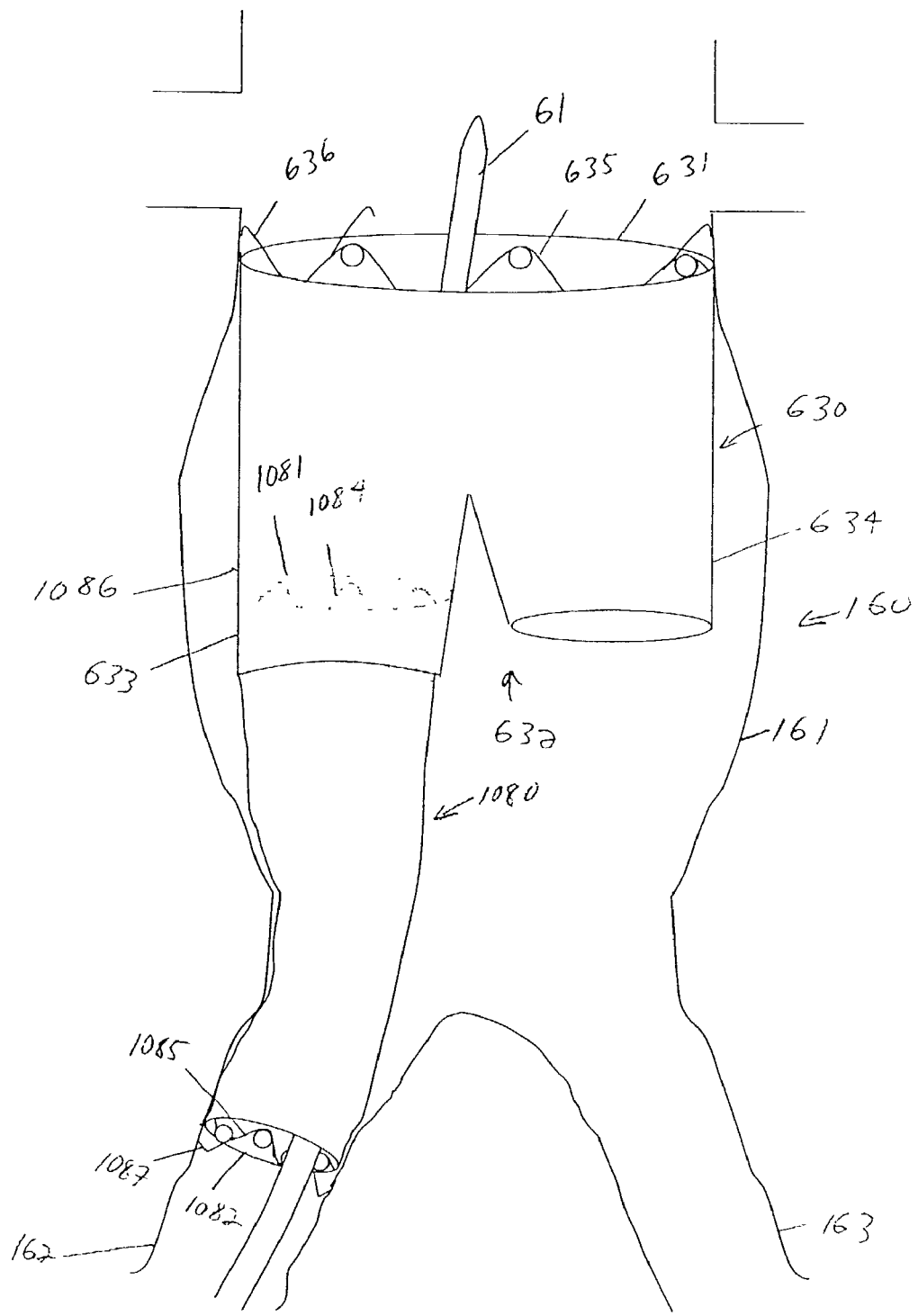
FIG. 23B is a side elevation, cross-sectional view of a limb component illustrated in FIG. 22 deployed within the ipsi-lateral limb support portion of the main body component and anchored within the ipsi-lateral branch of the vasculature.
Figure 23C:
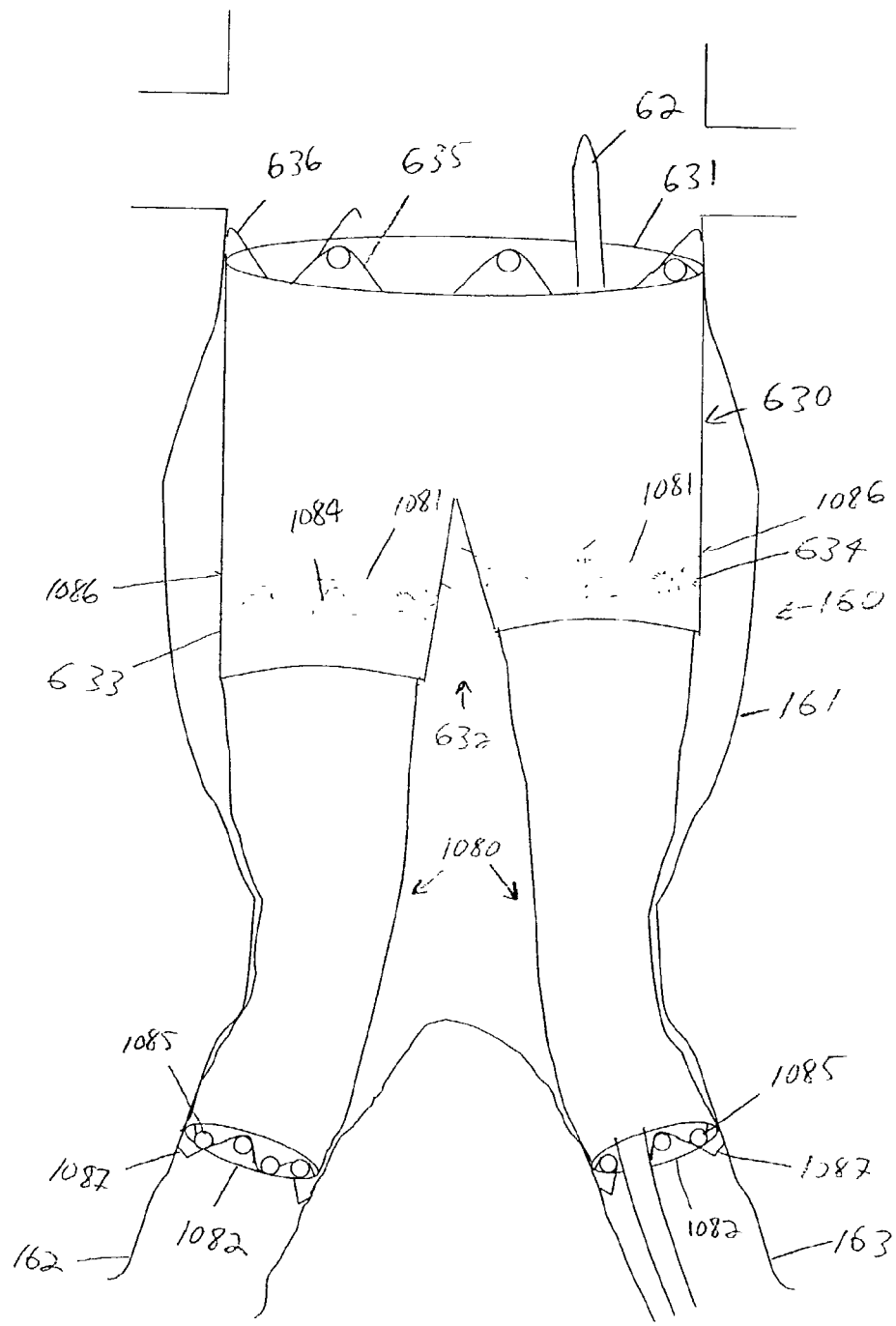
FIG. 23C is a side elevation, cross-sectional view of a limb component illustrated in FIG. 22 deployed within the contra-lateral limb support portion of the main body component and anchored within the contra-lateral branch of the vasculature.

Referring to FIGS. 23A to 23C, a method for in-situ assembly of a main body component 630 and two limb components 1080 of the embodiment of the invention shown in FIG. 22 is illustrated. It is contemplated that deployment of the main body component 630 and limb components 1080 may be accomplished using conduit-type catheters, releasable ties, or any other devices known in the art.

The main body component 630 is delivered in a compressed state to the desired location within the patient's vasculature 160 utilizing a catheter 60. As shown in FIG. 23A, the main body component 630 is deployed with the frame 635 proximal the aneurysm 161 and the hooks 636 embedded in the vessel wall.

Next, the ipsi-lateral limb support portion 633 is snared and a catheter 61 is introduced to deploy a limb component 1080 within the ipsi-lateral branch 162 of the vasculature 160. With the proximal end 1081 of the compressed limb component 1080 located within the ipsi-lateral limb support portion 633, the proximal frame 1084 is deployed as shown in FIG. 23B. Upon expansion of the frame 1084, the hooks 1086 are embedded in the graft material of the ipsi-lateral limb support portion 633, thereby securing the limb component 1080 to the main body component 630. Thereafter, the distal frame 1085 of the limb component 1080 is deployed, embedding the hooks 1087 into the vessel wall and securing the distal end 1082 within the ipsi-lateral branch 162 of the vasculature 160. By varying the position of the limb component 1080 within the limb support portion 633, the relative length of the ipsi-lateral limb component 1080 maybe varied.

Finally, the contra-lateral limb support portion 634 is snared and a catheter 62 is introduced into the contra-lateral branch 163 of the vasculature 160. As shown in FIG. 23C, another limb component 1080 is deployed within the contra-lateral limb support portion 634 of the main body component 630. By varying the position of the limb component 1080 within the limb support portion 634, the relative length of the contra-lateral limb component 1080 may also be varied.

Figure 24:
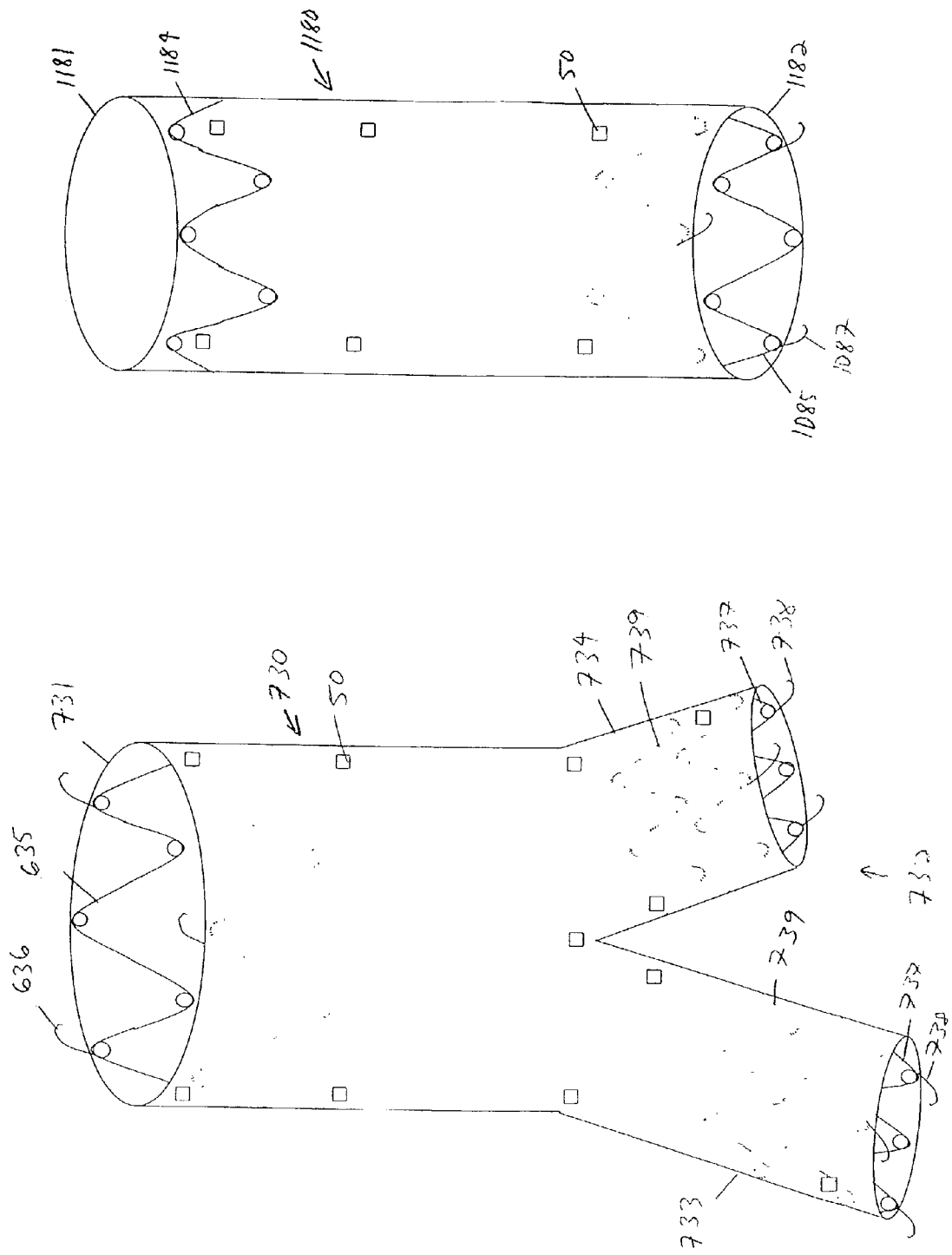
FIG. 24 is a perspective view, depicting an alternate embodiment of the limb component and main body component illustrated in FIG. 22.

As shown in FIG. 24, an alternate embodiment of the invention shown in FIG. 22 is illustrated. In many ways, the embodiment of the invention illustrated in FIG. 24 is similar to the embodiment illustrated in FIG. 22. However, the embodiment illustrated in FIG. 24 utilizes limb support portions that are deployed within the limb components for in-situ assembly. The main body component 730 is defined by a proximal end 731 and distal end 732. The limb component 1180 is defined by a proximal end 1181 and distal end 1182.

Similar to the embodiment illustrated in FIG. 22, the proximal end 731 of the main body component 730 has a frame 635 with caudal hooks or barbs 636 designed to be attached to the vessel wall and the distal end 732 has two limb support portions 733, 734 designed to receive the proximal end 1181 of the limb component 1180. Unlike the embodiment shown in FIG. 22, each limb support portion 733, 734 also has a frame 737 with hooks or barbs 738 designed to be attached to the proximal end 1181 of the limb component 1180. Also, the limb support portions 733, 734 may have a support frame 739. In a preferred embodiment, three V-hooks 738 are spaced 120° apart around the circumference of the distal frames 737.

The proximal end 1181 of the limb component 1180 is designed to receive a limb support portion 733, 734 of the main body component 730 and has a support frame 1184. In a preferred embodiment, the support frame 1184 is sewn to the graft material and made of Elgiloy®.

Referring to FIGS. 25A to 25E, a method for in-situ assembly of a limb component 1180 and main body component 730 of the embodiment of the invention shown in FIG. 24 is illustrated. It is contemplated that any devices known in the art may be used to deliver and deploy the main body component 730 and limb portion 1180.

Figure 25A:
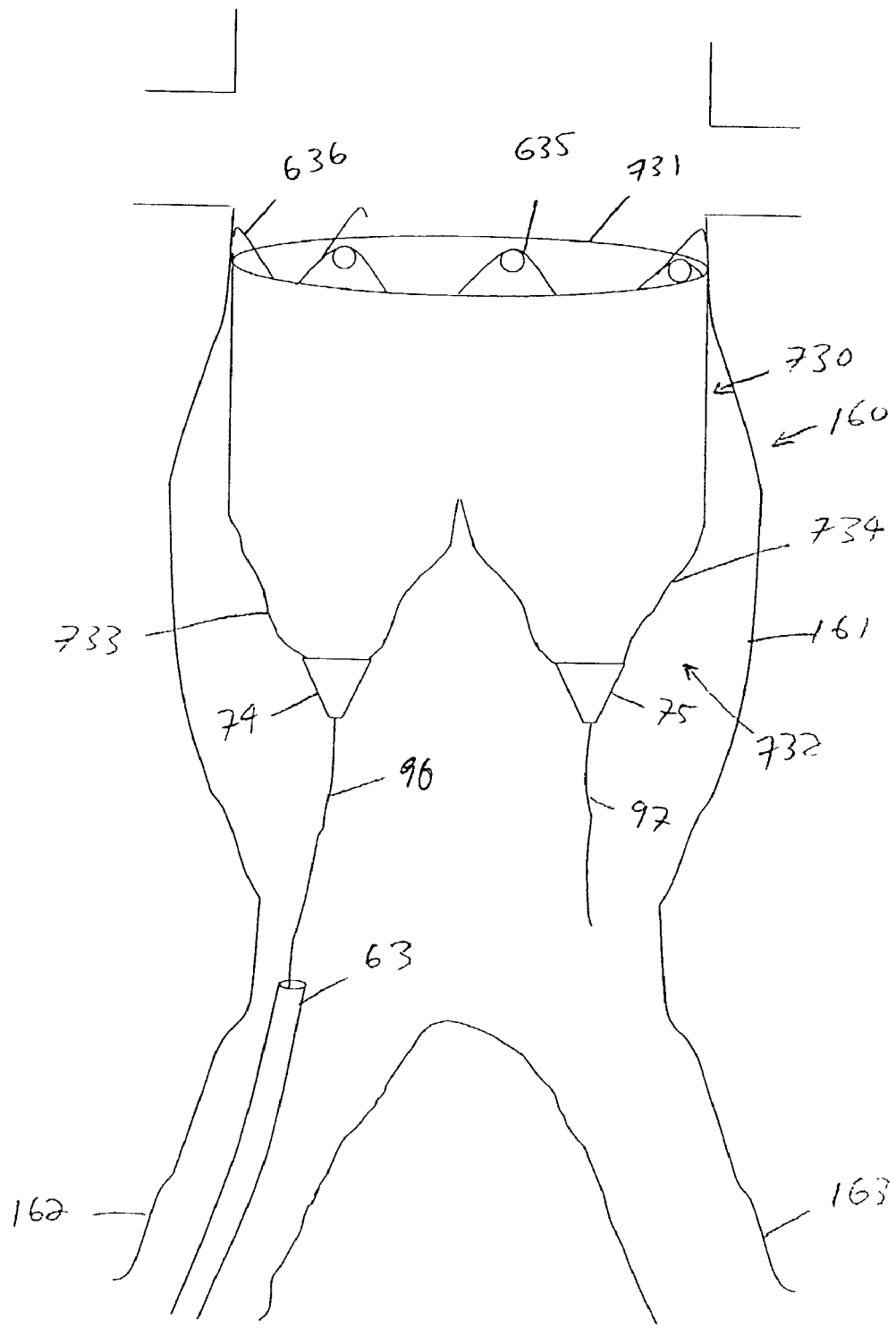
FIG. 25A is a side elevation, cross-sectional view of the main body component illustrated in FIG. 24 implanted at the treatment site with the limb support portions compressed within capsules.

The main body component 730 is delivered in a compressed state to the desired location within the patient's vasculature 160 utilizing a catheter 63. As shown in FIG. 25A, the main body component 730 is deployed with the frame 635 proximal the aneurysm 161 and the hooks 636 embedded in the vessel wall. The ipsi-lateral 733 and contra-lateral 734 limb support portions are not deployed, the distal frames 737 and hooks 738 compressed within capsules 74, 75 to which tethers 96, 97, respectively, are attached.

Figure 25B:
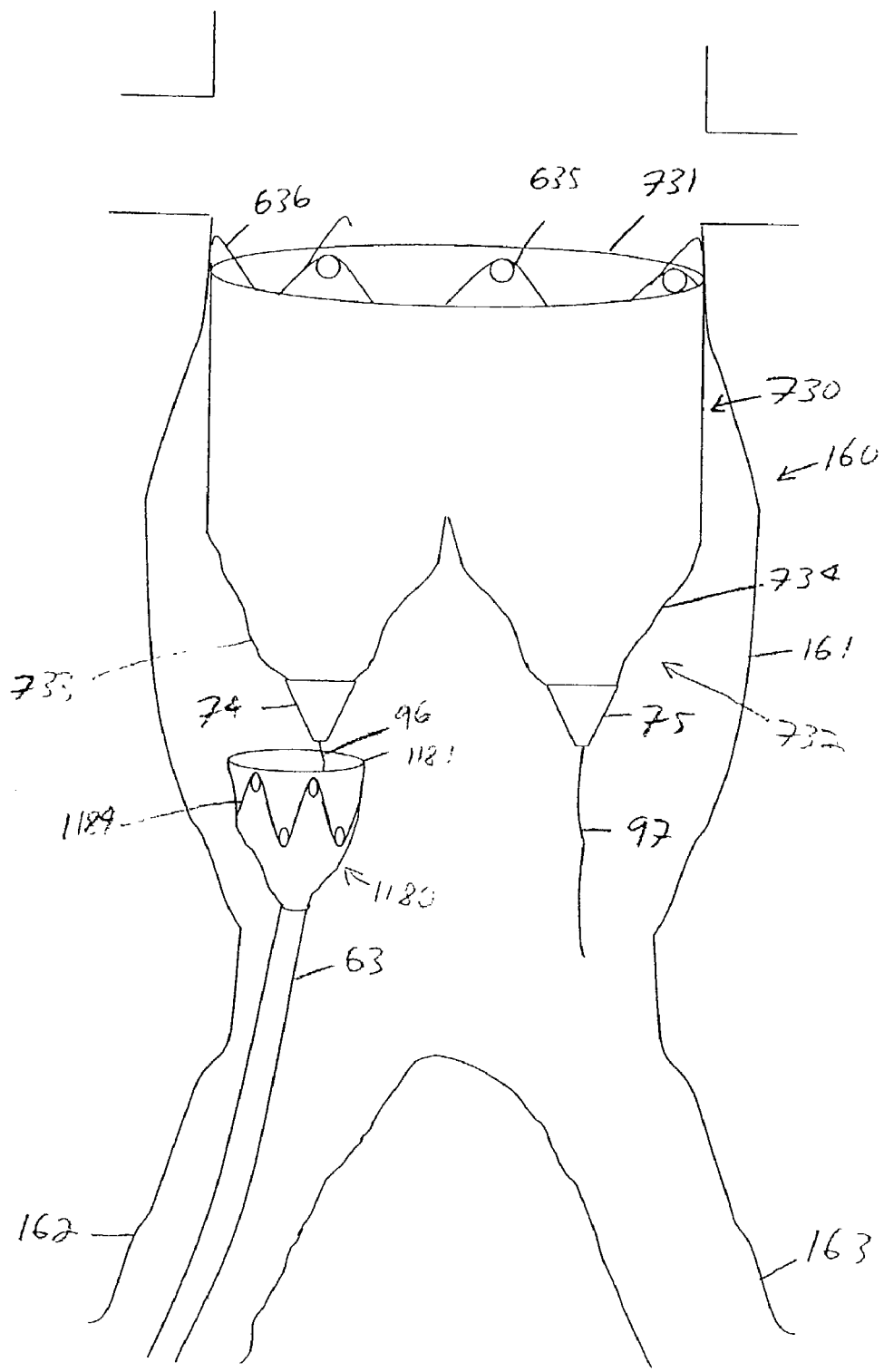
FIG. 25B is a side elevation, cross-sectional view of a limb component illustrated in FIG. 24 partially deployed.

Next, the tether 96 attached to the capsule 74 holding the compressed ipsi-lateral limb support portion 733 frame 737 and hooks 738 is snared and held taut. A limb component 1180 is then partially deployed and advanced proximally toward the capsule 74, as shown in FIG. 25B.

Figure 25C:
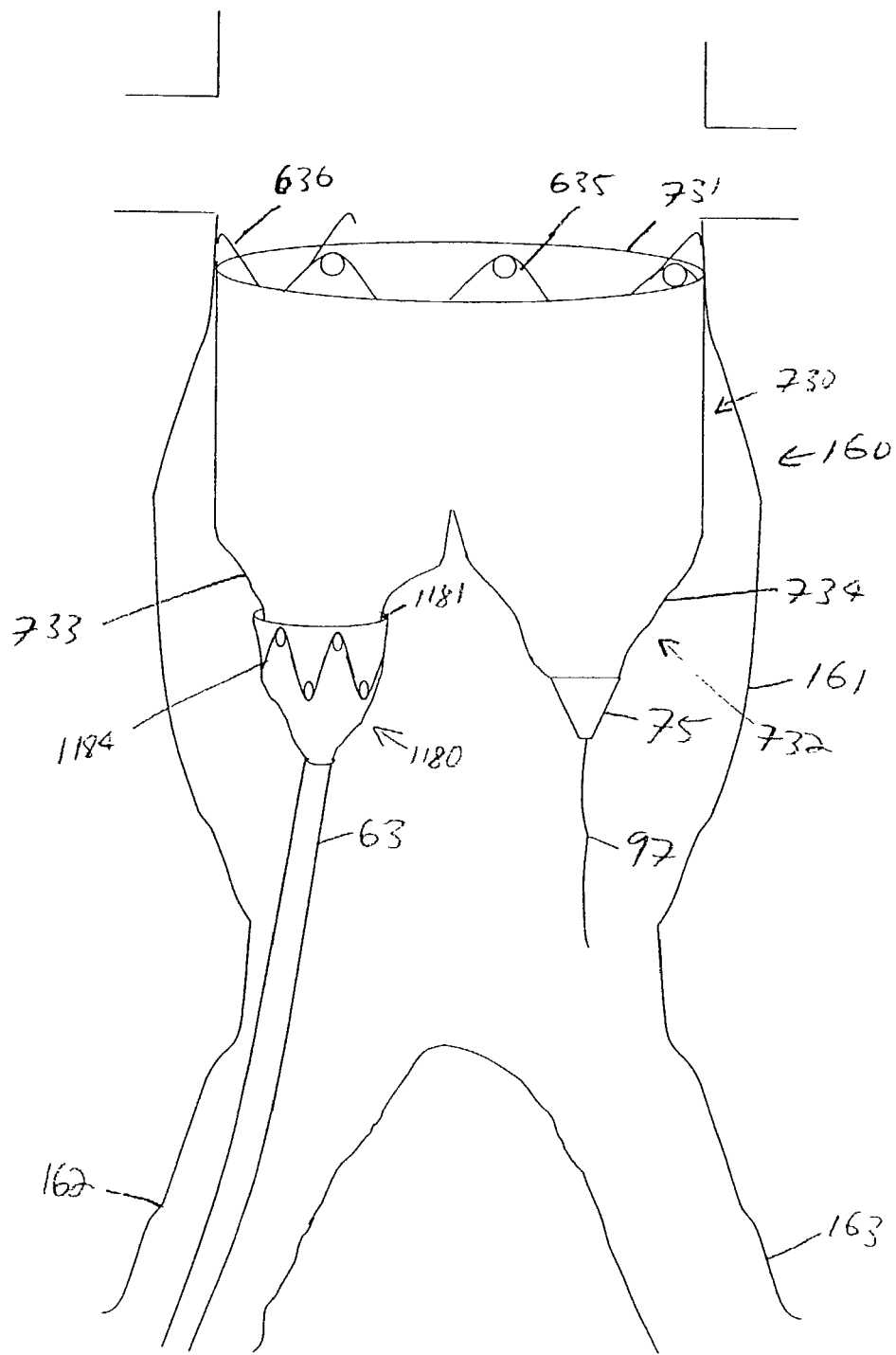
FIG. 25C is a side elevation, cross-sectional view of a limb component illustrated in FIG. 24 partially deployed and advanced over the ipsi-lateral capsule of the main body component.

As shown in FIG. 25C, the partially-deployed limb component 1180 is then advanced over the capsule 74 holding the compressed ipsi-lateral limb support portion 733 frame 737 and hooks 738. The partially-deployed limb support portion 1180 is advanced until the desired limb component 1180 relative length is achieved, keeping in mind the landing area required in order to deploy the distal frame 1085 and embed the hooks 1087 in the wall of the ipsi-lateral branch 162 of the vasculature 160.

Figure 25D:
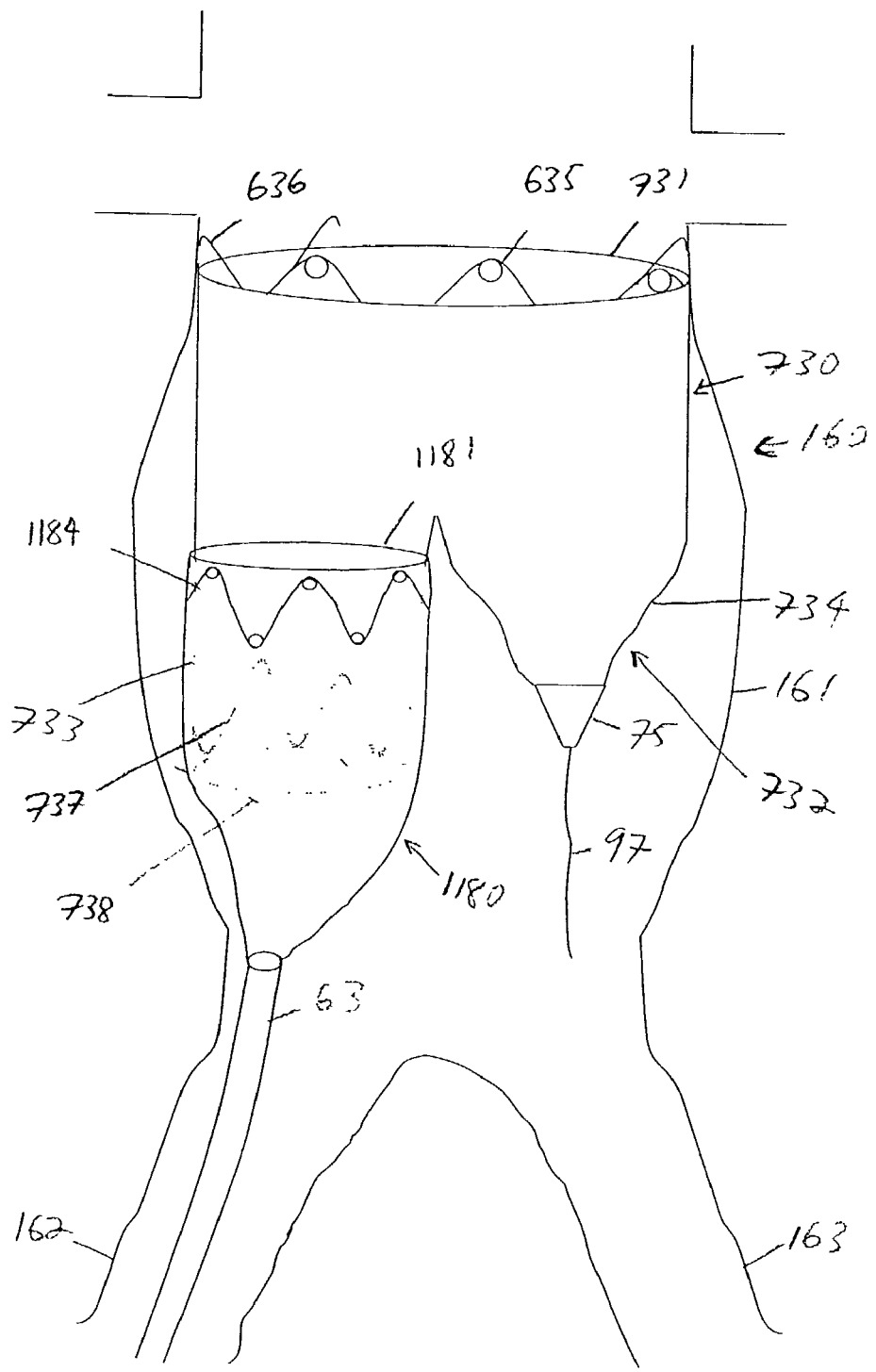
FIG. 25D is a side elevation, cross-sectional view of a limb component illustrated in FIG. 24 partially deployed and the ipsi-lateral limb support portion of the main body component deployed within the proximal end at the limb component.

Once the desired relative length of the ipsi-lateral limb component 1180 is achieved, the distal frame 737 of the ipsi-lateral limb support portion 733 is deployed inside the proximal end 1181 of the limb component 1180 as shown in FIG. 25D. Upon expansion of the frame 737, the hooks 738 are embedded in the graft material of the limb component 1180, thereby securing the limb component 1180 to the main body component 730.

Figure 25E:
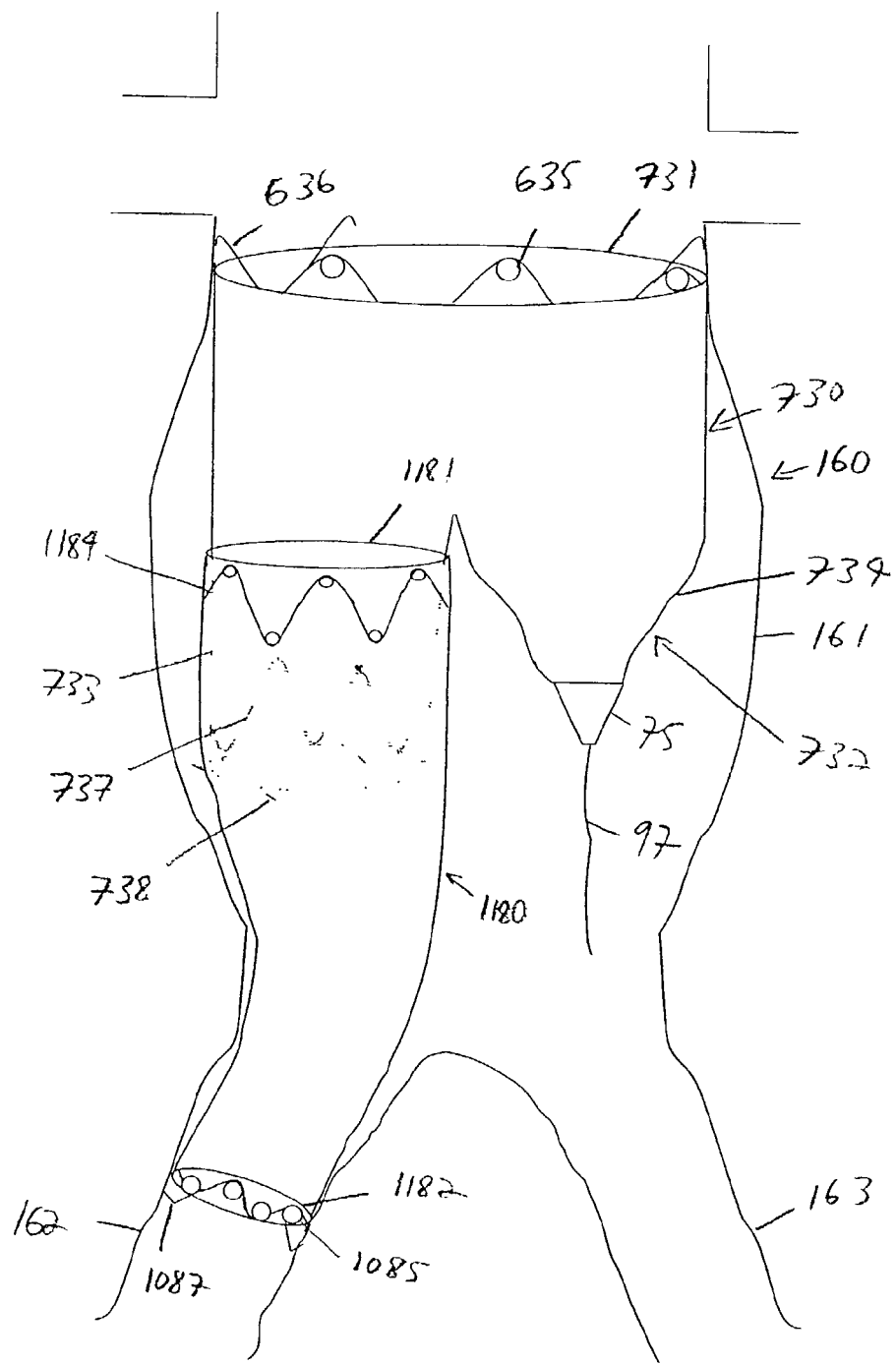
FIG. 25E is a side elevation, cross-sectional view of a limb component illustrated in FIG. 24 joined to the main body component and anchored within the ipsi-internal branch of the vasculature.

Next, as shown in FIG. 25E, the distal frame 1085 of the limb component 1180 is deployed, embedding the hooks 1087 into the lumen wall and securing the distal end 1182 of the limb component 1180 within the ipsi-lateral branch 162 of the vasculature 160. By varying the position of the limb component 1180 within the limb support portion 733, the relative length of the ipsi-lateral limb component 1180 may be varied.

Delivery and deployment of a contra-lateral limb component 1180 is accomplished by a method similar to that illustrated in FIGS. 25A to 25E. A catheter (not shown) is advanced proximally in the contra-lateral branch 163 of the vasculature 160 to snare the tether 97 attached to the capsule 75 holding the compressed contra-lateral limb support portion 734 frame 737 and hooks 738. With the tether 97 held taut, another limb component 1180 is partially deployed and advanced proximally toward the capsule 75 until the desired relative length of the contra-lateral limb component 1180 is achieved. The distal frame 737 of the contra-lateral limb support portion 734 is then deployed inside the proximal end 1181 of the limb component 1180, thereby embedding the hooks 738 in the graft material of the limb component 1180 and securing the limb component 1180 to the main body component 730. The distal fame 1085 of the limb component 1180 is then deployed, embedding the hooks 1087 in the contra-lateral branch 163 of the vasculature 160.

The depiction of the various frames 635, 1084, 1085, 737, 1184 and hooks 636, 1086, 1087, 738 in FIGS. 22-25 is for illustration purposes only. It is contemplated that the frames 635, 1084, 1085, 737, 1184 maybe located internal or external the graft material and may be of any type known within the art. It is further contemplated that the frames 635, 1084, 1085, 737, 1184 may be self-expanding or a balloon may be utilized. Moreover, it is contemplated that all the methods of strengthening the joint between a limb component and main body component depicted herein and materials specified for the components are applicable to the embodiments of the invention illustrated in FIGS. 22 and 24. For example, multiple limb components may be "chained" together, tufting may be utilized to strengthen the seal between the components, and the graft material may be reinforced with a coating or by altering the weave pattern.

Thus, it will be apparent from the foregoing that, while particular forms of the invention have been illustrated and described, various modifications can be made without the parting from the spirit and scope of the invention. For example, both the main graft component and the limb components can have various configurations including tubular, flared, bifurcated and trifurcated forms. Accordingly, it is not intended that the invention be limited, except as by the appended claims.

What is claimed is:

1. A modular endovascular graft device for treating vasculature, comprising:

a first graft component having a first wall with proximal and distal ends, the proximal end configured to be implanted and embedded within vasculature, the distal end having a plurality of pre-fabricated holes; and a second graft component having a longitudinal axis and a second wall with proximal and distal ends, the proximal end having a frame with a plurality of radially extending components positioned on a side of the second wall opposite from an inside region defined by the second wall and said plurality of radially extending components extend beyond the second wall to enable attachment of the second component to the first implanted and embedded component, at least one of the plurality of radially extending components is configured to extend outwardly away from the longitudinal axis of the second component to penetrate through at least one of said pre-fabricated holes and embed in the distal end of the first wall.

2. The device of claim 1, the first component further comprising a frame with a plurality of radially extending components at the proximal end.

3. The device of claim 1, the second component further comprising a frame with a plurality of radially extending components at the distal end.

4. The device of claim 1, wherein the frame is in the form of a self-expanding stent.

5. The device of claim 1, wherein the frame is external the graft component.

6. The device of claim 1, wherein the frame is internal the graft component.

7. The device of claim 1, wherein the plurality of radially extending components are in the form of hooks or barbs.

8. The device of claim 7, wherein the hooks or barbs have sharpened points.

9. The device of claim 7, wherein the hooks or barbs are pointed in a caudal direction.

10. The device of claim 1, the first graft component further comprising at least one limb support section at the distal end.

11. The device of claim 1, wherein the first graft component is bifurcated.

12. The device of claim 1, wherein the first graft component is trifurcated.

13. The device of claim 1, wherein at least one of the first and second graft components has a generally tubular configuration.

14. The device of claim 1, wherein at least one of the first and second graft components has a flared configuration.

15. The device of claim 1, wherein at least one of the first and second graft components has a tapered configuration.

16. The device of claim 1, further comprising fuzzy tufts of yarn configured at a junction between the first and second components.

17. The device of claim 1, the first component further comprising radiopaque markers.

18. The device of claim 1, the second component further comprising radiopaque markers.

19. The device of claim 1, the first component further comprising at least one support frame at the distal end.

20. The device of claim 1, further comprising additional graft components, each having a wall and including a frame with a plurality of radially extending components which, upon assembling each additional component and the previously assembled components, at least one of the plurality of radially extending components extend through the wall of at least one of the previously assembled components such that a successive chain of assembled components is formed.

21. A modular endovascular graft device for treating vasculature, comprising:

a first graft component having a longitudinal axis, a first wall with proximal and distal ends, the proximal end configured to be implanted and embedded within vasculature and the distal end having a frame with a plurality of radially extending components positioned on a side of the first wall opposite from an inside region defined by the first wall and that extend beyond the first wall; and a second graft component having a second wall with proximal and distal ends, the proximal end having a plurality of pre-fabricated holes configured to be disposed over at least a portion of the distal end of the first component, to enable attachment of the second component to the first partially-implanted and embedded first component, at least one of the plurality of radially extending components of the first component is configured to extend outwardly away from the longitudinal axis of the first component to penetrate through at least one of said pre-fabricated holes and embed in the second wall of the second component.

22. The device of claim 21, the first component further comprising a frame with a plurality of radially extending components at the proximal end.

23. The device of claim 21, the first component further comprising a support frame at the distal end.

24. The device of claim 21, the second component further comprising a frame with a plurality of radially extending components at the distal end.

25. The device of claim 21, wherein the frame is in the form of a self-expanding stent.

26. The device of claim 21, wherein the frame is external the graft component.

27. The device of claim 21, wherein the frame is internal the graft component.

28. The device of claim 21, the second component further comprising a support frame at the proximal end.

29. The device of claim 21, wherein the plurality of radially extending components are in the form of hooks or barbs.

30. The device of claim 29, wherein the hooks or barbs have sharpened points.

31. The device of claim 30, wherein the hooks or barbs are pointed in a caudal direction.

32. The device of claim 21, wherein the first graft component is bifurcated.

33. The device of claim 21, wherein the first graft component is trifurcated.

34. The device of claim 21, wherein the second graft component has a generally tubular configuration.

35. The device of claim 21, wherein the second graft component has a flared configuration.

36. The device of claim 21, wherein the second graft component has a tapered configuration.

37. The device of claim 21, further comprising fuzzy tufts of yarn configured at a junction between the first and second components.

38. The device of claim 21, the first component further comprising radiopaque markers.

39. The device of claim 21, the second component further comprising radiopaque markers.

* * * * *